United States Patent
Fairlie et al.

(10) Patent No.: US 8,921,306 B2
(45) Date of Patent: Dec. 30, 2014

(54) NOCICEPTIN MIMETICS

(75) Inventors: David Fairlie, Mt. Ommaney (AU); Rosemary Sharon Harrison, Bondi Junction (AU); Nicholas Evan Shepherd, Blackburn North (AU)

(73) Assignee: The University of Queensland, Queensland (AU)

( * ) Notice: Subject to any disclaimer, the term of this patent is extended or adjusted under 35 U.S.C. 154(b) by 0 days.

(21) Appl. No.: 13/702,479

(22) PCT Filed: Jun. 7, 2011

(86) PCT No.: PCT/AU2011/000707
§ 371 (c)(1),
(2), (4) Date: Feb. 27, 2013

(87) PCT Pub. No.: WO2011/153583
PCT Pub. Date: Dec. 15, 2011

(65) Prior Publication Data
US 2013/0157928 A1    Jun. 20, 2013

(30) Foreign Application Priority Data
Jun. 7, 2010 (AU) ................. 2010902481

(51) Int. Cl.
| | |
|---|---|
| *A61K 38/10* | (2006.01) |
| *A61K 45/06* | (2006.01) |
| *C07K 7/08* | (2006.01) |
| *A61P 11/00* | (2006.01) |
| *A61P 11/06* | (2006.01) |
| *A61P 11/16* | (2006.01) |
| *A61P 13/00* | (2006.01) |
| *A61P 13/02* | (2006.01) |
| *A61P 15/00* | (2006.01) |
| *A61P 15/10* | (2006.01) |
| *A61P 1/00* | (2006.01) |
| *A61P 25/00* | (2006.01) |
| *A61K 38/12* | (2006.01) |
| *C07K 7/60* | (2006.01) |
| *A61K 38/00* | (2006.01) |

(52) U.S. Cl.
CPC ................. *A61K 38/10* (2013.01); *A61K 38/00* (2013.01); *A61K 45/06* (2013.01); *A61K 38/12* (2013.01); *C07K 7/08* (2013.01); *C07K 7/60* (2013.01)
USPC ......... 514/1.4; 514/15.4; 514/15.6; 514/15.7; 514/16.4; 514/17.5; 514/17.6; 514/17.7; 514/18.4; 514/1.5; 514/1.7; 514/4.9; 514/5.2; 514/6.9; 530/300; 530/326

(58) Field of Classification Search
CPC ........... C07K 7/08; C07K 7/60; A61K 38/00; A61K 38/10; A61K 45/06; A61K 38/12
USPC .......... 514/15.4, 15.6, 15.7, 16.4, 17.5, 17.6, 514/17.7, 18.4, 1.4, 1.5, 1.7, 4.9, 5.2, 6.9; 530/326, 300
See application file for complete search history.

(56) References Cited

FOREIGN PATENT DOCUMENTS

| | | | | |
|---|---|---|---|---|
| WO | 99/03880 | 1/1999 | | |
| WO | 2005/090388 | 9/2005 | | |
| WO | WO 2005090388 A1 * | 9/2005 | ............... | C07K 7/50 |
| WO | 2011/153583 | 12/2011 | | |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Charoenchai et al., "High Affinity Conformationally Constrained Nociceptin/Orphanin FQ(1-13) Amide Analogues," Journal of Medicinal Chemistry, 2008, 51:4385-4387.
Green & Wutz, Protective Groups in Organic Synthesis, 3rd Edition, John Wiley & Sons, 1999, TOC ONLY, Will provide specific passages upon Examiner request.
Guerrini et al., 2000, "Further Studies on Nociceptin-Related Peptides: Discovery of a New Chemical Template with Antagonist Activity on the Nociceptin Receptor," J. Med. Chem., 43:2805-2813.
Guerrini et al., "N- and C-Terminal Modifications of Nociceptin/Orphanin FQ Generate Highly Potent NOP Receptor Ligands," 2005, J. Med. Chem., 48:1421-1427.
Harrison et al., "Downsizing human, bacterial, and viral proteins to short water-stable alpha helices that maintain biological potency," Proceedings of the National Academy of Science, 2010, vol. 107, pp. 11686-11691.
Harrison et al., "Novel Helix-Constrained Nociceptin Derivatives Are Potent Agonists and Antagonists of ERK Phosphorylation and Thermal Analgesia in Mice," Journal of Medicinal Chemistry, 2010, 53:8400-8408.
Kaiser et al., "Color Test of Detection of Free Terminal Amino Groups in the Solid-Phase Synthesis of Peptides," 1970, Anal. Biochem. 34:595-598.
Marion & Wuthrich, "Application of Phase Sensitive Two-Dimensional Correlated Spectroscopy (COSY) for Measurements of 1H-1H Spin-Spin Coupling Constants in Proteins," 1983, Biochem. Biophys. Res. Commun., 113:967-974.

(Continued)

*Primary Examiner* — Julie Ha
*Assistant Examiner* — Erinne Dabkowski
(74) *Attorney, Agent, or Firm* — Casimir Jones S.C.

(57) ABSTRACT

The present invention relates to nociceptin peptide mimetics that have α-helical structures and bind to and modulate the opioid receptor-like-1 (ORL-1) receptor. The peptide mimetics are constrained cyclic nociceptin analogs which have either agonist or antagonist activity. Pharmaceutical compositions comprising the nociceptin peptide mimetics and methods of treating or preventing a disease or condition ameliorated by modulating the ORL-1 receptor are also described.

22 Claims, 1 Drawing Sheet

(56) References Cited

OTHER PUBLICATIONS

Piotto et al., "Gradient-tailored excitation for single-quantum NMR spectroscopy of aqueous solutions," 1992, J. Biomol. NMR, 2:661-665.

Taylor, "The Synthesis and Study of Side-Chain Lactam-Bridged Peptides," 2002, Biopolymers, 66:49-75.

Wider & Dreier, "Measuring Protein Concentrations by NMR Spectroscopy," 2006, J. Am. Chem. Soc. 128:2571-2576.

International Search Report, mailed Jul. 11, 2011, for International Patent Application No. PCT/AU2011/000707, 12 pages.

Chang et al., "Structure—activity studies on different modifications of nociceptin/orphanin FQ: Identification of highly potent agonists and antagonists of its receptor," Regulatory Peptides 130 (2005) 116-122.

Orsini et al., "The Nociceptin Pharmacophore Site for Opioid Receptor Binding Derived from the NMR Structure and Bioactivity Relationships," J Biol Chem, 2005, 280:8134-8142.

Arudin et al., "Synthesis and biological activity of nociceptin/orphanin FQ analogues substituted in position 7 or 11 with Calpha,aplha-dialkylated amino acids," Bioorganic & Medicinal Chemistry, 2007, 15:4434-4443.

Kitayama et al., "Pharmacological profile of the cyclic nociceptin/orphanin FQ analogues c[Cys10,14]N/OFQ(1-14) NH2 and c[Nphe1,Cys10,14]N/OFQ(1-14)NH2," Naunyn-Schmiedeberg's Archives of Pharmcology, 2003, 368:528-537.

Kitayama et al., "In vitro pharmacological characterisation of a novel cyclic nociceptin/orphanin FQ analogue c [Cys7,10]N/OFQ(1-13)NH2," Naunyn-Schmiedeberg's Archives of Pharmcology, 2007, 375:369-376.

Mastuzza and Bastanzio, "Development of Nociceptin Receptor (NOP) Agonists and Antagonists," Medicinal Research Reviews, 2011, 31:605-648.

Schmidt et al., "Structure-Activity Relationships of Linear Cyclic Nociceptin Analogs and Conformational Analysis by CD and NMR Spectroscopy," Peptides: The Wave of the Future, Proceedings of the 2nd Int. Peptide Symposium in conjuction with the 17th American Peptide Symposium, 2001, San Diego, CA, pp. 685-686.

Tancredi et al., "The Interaction of Highly Helical Structural Mutants with the NOP Receptor Discloses the Role of the Address Domain of Nociceptin/Orphanin FQ," Chem Eur J, 2005, 11:2061-2070.

Zhang et al., "Novel, Potent ORL-1 Receptor Agonist Peptides Containing alpha-Helix-Promoting Conformational Constraints," J Med Chem, 2002, 45:5280-5286.

Extended European Search Report for EP11791746.8, mailed Jul. 11, 2014, 10 pages.

\* cited by examiner

NOCICEPTIN MIMETICS

This application is a §371 National Entry of International Application No. PCT/AU2011/000707, filed Jun. 7, 2011, which is incorporated herein by reference and which claims the benefit of Australian Patent Application No. 2010902481, filed Jun. 7, 2010.

FIELD OF THE INVENTION

The present invention relates to nociceptin peptide mimetics that have α-helical structures and bind to and modulate the opioid receptor-like-1 (ORL-1) receptor, also known as the nociceptin opioid peptide receptor (NOR or NOP receptor). The peptide mimetics are constrained nociceptin analogues which have ORL-1 agonist or antagonist activity. Pharmaceutical compositions comprising the nociceptin peptide mimetics and methods of treating or preventing a disease or condition ameliorated by modulating ORL-1 receptor are also described.

BACKGROUND OF THE INVENTION

Nociceptin, also known as Orphanin FQ, is a peptide of 17 amino acid residues that binds to the ORL-1 receptor and has the amino acid sequence:

```
                                      SEQ ID NO: 1
        FGGFTGARKSARKLANQ
``` where the N-terminus (left hand side) is a free amine and the C-terminus (right hand side) is a free carboxylic acid.

ORL-1 is a GPCR having high sequence homology with other opioid receptors. Nociceptin and the ORL-1 receptor are widely distributed in the brain and central nervous system (CNS), as well as in the periphery. Among different roles including pain regulation, analgesia, tolerance and withdrawal, learning, memory, food intake, anxiety and mood, psychiatric disorders, motor function and locomotion, nociception, neuronal functions, cardiovascular and respiratory stress, and ill defined roles in inflammation, immunostimulation and immunity, have been attributed to nociceptin and the ORL-1 receptor.

Nociceptin(1-17) is composed of an N-terminal "message" tetrapeptide domain FGGF (amino acid residues 1-4) that activates the receptor, linked to a C-terminal "address" domain, (amino acid residues 7-17), that provides high affinity and selectivity for the receptor. The address domain of nociceptin contains key basic amino acid residues that likely bind acidic residues within the second extracellular loop of the ORL-1 receptor.

To date, no three-dimensional structure of the ORL-1 G protein-coupled receptor, either in complex with ligands or alone, is available. However, the solution structure of nociceptin has been investigated by CD and NMR spectroscopies, showing some helical structure from residues 4-17 under conditions that to some extent simulate a membrane environment (aqueous sodium dodecylsulphate (SDS) micelles) (Orsini et al., 2005, *J. Biol. Chem.* 280: 8134-8142). On the other hand, in water alone this peptide allows no discernible three dimensional structure by CD or NMR spectroscopy.

Nociceptin peptide analogues with ORL-1 receptor agonist or antagonist activity have potential therapeutic uses, and identification, of peptides having high binding affinity and functional activity as well as stability to proteolytic breakdown are required.

SUMMARY OF THE INVENTION

The present invention is predicated in part on the discovery that use of an optimized helix-inducing cyclization strategy can convert nociceptin peptide, analogues into highly potent agonist ($EC_{50}$ 40 pM) and antagonist ($IC_{50}$ 10 nM) compounds for modulating ORL-1 receptor function and with improved serum stability over unconstrained peptides. This enhanced potency relative to nociceptin itself is due to the pre-organization of the peptide analogues in highly alpha helical structures that are stable in aqueous media, unlike nociceptin which shows negligible alpha helical structure in the same environment.

In one aspect of the present invention there is provided a peptide of formula (I):

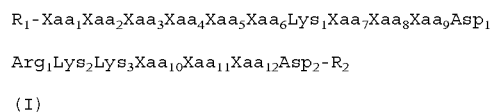

$$R_1\text{-}Xaa_1Xaa_2Xaa_3Xaa_4Xaa_5Xaa_6Lys_1Xaa_7Xaa_8Xaa_9Asp_1$$
$$Arg_1Lys_2Lys_3Xaa_{10}Xaa_{11}Xaa_{12}Asp_2\text{-}R_2$$

(I)

wherein
$Xaa_1$ is Phe or N-BzlGly;
$Xaa_2$ is Gly;
$Xaa_3$ is Gly or Ala;
$Xaa_4$ is Phe or 4-$R_3$-Phe;
$Xaa_5$ is Thr or Ser;
$Xaa_6$ is any amino acid residue;
$Xaa_8$ is a basic amino acid residue;
$Xaa_7$, $Xaa_9$, $Xaa_{10}$, $Xaa_{11}$ and $Xaa_{12}$ are independently selected from any amino acid residue;
$R_1$ is hydrogen or an N-terminal capping group; with the proviso that when $Xaa_1$ is N-BzlGly, $R_1$ is absent;
$R_2$ is —OH or a C-terminal capping group; and
$R_3$ is an electron withdrawing substituent;
wherein the side chains of $Lys_1$ and $Asp_1$ are linked to form a lactam bridge and the side chains of $Lys_3$ and $Asp_2$ are linked to form a lactam bridge;
or a pharmaceutically acceptable salt thereof.

In another aspect of the invention, there is provided a pharmaceutical composition comprising a peptide of formula (I) or a pharmaceutically acceptable salt thereof and a pharmaceutically acceptable carrier or excipient.

In yet another aspect of the invention, there is provided a method of treating or preventing a disease or disorder ameliorated by modulation of the ORL-1 receptor comprising administering to a subject, an effective amount of a peptide of formula (I) or a pharmaceutically acceptable salt thereof.

In some embodiments the peptides of formula (I) are ORL-1 receptor agonists and in other embodiments, the peptides of formula (I) are ORL-1 receptor antagonists.

DESCRIPTION OF THE INVENTION

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described.

The articles "a" and "an" are used herein to refer to one or to more than one (i.e. to at least one) of the grammatical object of the article. By way of example, "an element" means one element or more than one element.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein "alpha helical" refers to a three dimensional structural conformation which is analogous to those found in proteins and polypeptides. The alpha helix conformation found in naturally occurring proteins and polypeptides has its side chains extending to the outside of the structure, has a complete turn every 3.6 amino acids, is right-handed and typically has hydrogen bonding between the carbonyl groups of the amide bond and an amide N—H group 4 amino acids further along in the sequence so that there are three amino acid residues intervening between the hydrogen bonding amide carbonyl and its partnering hydrogen bonding NH proton. The nociceptin peptide mimetics of the present invention can be characterized by their molar elipticities obtained from circular dichroism spectroscopy (CD spectroscopy), from which alpha helical content can be measured at $\lambda=222$ nm and expressed as a percentage of the theoretical helicity obtainable for that peptide or a relative helicity compared to a reference standard or standard helix.

As used herein, the term "amino acid" refers to compounds having an amino group and a carboxylic acid group. An amino acid may be a naturally occurring amino acid or non-naturally occurring amino acid and may be a proteogenic amino acid or a non-proteogenic amino acid Suitable naturally occurring proteogenic amino acids are shown in Table 1 together with their one letter and three letter codes.

TABLE 1

| Amino Acid | one letter code | three letter code |
| --- | --- | --- |
| L-alanine | A | Ala |
| L-arginine | R | Arg |
| L-asparagine | N | Asn |
| L-aspartic acid | D | Asp |
| L-cysteine | C | Cys |
| L-glutamine | Q | Gln |
| L-glutamic acid | E | Glu |
| glycine | G | Gly |
| L-histidine | H | His |
| L-isoleucine. | I | Ile |
| L-leucine | L | Leu |
| L-lysine | K | Lys |
| L-methionine | M | Met |
| L-phenylalanine | F | Phe |
| L-proline | P | Pro |
| L-serine | S | Ser |
| L-threonine | T | Thr |
| L-tryptophan | W | Trp |
| L-tyrosine | Y | Tyr |
| L-valine | V | Val |

As used herein, "amino acid side chain" or "side chain" refers to the characterizing substituent of the amino acid. This term refers to the substituent bound to the α-carbon of either a natural or non-natural α-amino acid. For example, the characterizing substituents of some naturally occurring amino acids are shown in Table 2.

TABLE 2

The Proteinogenic Amino Acids

| Amino acid | —R |
| --- | --- |
| Alanine | —$CH_3$ |
| Arginine | —$(CH_2)_3NHC(=NH)NH_2$ |
| Asparagine | —$CH_2CONH_2$ |
| Aspartic acid | —$CH_2CO_2H$ |
| Cysteine | —$CH_2SH$ |
| Glutamine | —$(CH_2)_2CONH_2$ |
| Glutamic acid | —$(CH_2)_2CO_2H$ |
| Glycine | —H |
| Histidine | —$CH_2$(4-imidazolyl) |
| Isoleucine | —$CH(CH_3)CH_2CH_3$ |
| Leucine | —$CH_2CH(CH_3)_2$ |
| Lysine | —$(CH_2)_4NH_2$ |
| Methionine | —$(CH_2)_2SCH_3$ |
| Phenylalanine | —$CH_2Ph$ |
| Serine | —$CH_2OH$ |
| Threonine | —$CH(CH_3)OH$ |
| Tryptophan | —$CH_2$(3-indolyl) |
| Tyrosine | —$CH_2$(4-hydroxyphenyl) |
| Valine | —$CH(CH_3)_2$ | and proline in which the R-group is bonded to the amino nitrogen to form a 5-membered ring.

Some non-limiting examples of non-naturally occurring of non-proteinogenic amino acids are shown in Table 3.

TABLE 3

Non-naturally occurring or Non-Proteinogenic Amino Acids

| Amino acid | —R |
| --- | --- |
| α-aminobutyric acid | —$CH_2CH_3$ |
| Ornithine (Orn) | —$(CH_2)_3NH_2$ |
| 2,3-diaminopropionic acid (Dap) | —$CH_2NH_2$ |
| 2,4-diaminobutanoic acid (Dab) | —$CH_2CH_2NH_2$ |
| norvaline | —$CH_2CH_2CH_3$ |
| Norleucine (Nle) | —$(CH_2)_3CH_3$ |
| homoarginine | —$(CH_2)_4NHC(=NH)NH_2$ |
| homolysine | —$(CH_2)_5NH_2$ |

Other non-proteinogenic amino acids that may be included are D-amino acids and L- or D-N-methyl amino acids. Examples of these amino acids include D-alanine, D-arginine, D-asparagine, D-aspartic acid, D-cysteine, D-glutamine, D-glutamic acid, D-histidine, D-isoleucine, D-leucine, D-lysine, D-methionine, D-phenylalanine, D-proline, D-serine, D-threonine, D-tryptophan, D-tyrosine, D-valine, L-N-methylalanine, L-αN-methylarginine, L-αN-methylasparagine, L-N-methylaspartic acid, L-N-methylcysteine, L-αN-methylglutamine, L-N-methylglutamic acid, N-methylglycine, L-αN-methyl-histidine, L-N-methylisoleucine, L-N-methylleucine, L-αN-methyllysine, L-N-methylmethionine, L-N-methylphenylalanine, L-αN-methylproline, L-N-methylserine, L-N-methylthreonine, L-N-methyltryptophan, L-N-methyltyrosine, L-N-methylvaline, D-N-methylalanine, D-αN-methylarginine, D-αN-methylasparagine, D-N-methylaspartic acid, D-N-methylcysteine, D-αN-methylglutamine, D-N-methylglutamic acid, D-αN-methylhistidine, D-N-isoleucine, D-N-methylleucine, D-αN-methyllysine, D-N-methylmethionine, D-N-phenylalanine, D-N-methylproline, D-N-methylserine, D-N-methylthreonine, D-N-methyltryptophan, D-N-methyltyrosine, D-N-methylvaline, D-α-aminobutyric acid, L-N-methyl-α-aminobutyric acid, D-N-methyl-α-aminobutyric acid, D-ornithine, L-αN-methylornithine, D-αN-methylornithine, D-2,3-diaminopropionic acid, L-2N-methyl-2,3-diaminopropionic acid, D-2N-methyl-2,3-diaminopropionic acid, D-2,4-diaminobutanoic acid, L-2N-methyl-2,4-diaminobutanoic acid, D-2N-methyl-2,4-diaminobutanoic acid, D-norvaline, L-N-methylnorvaline, D-N-methylnorvaline, D-norleucine, L-N-methylnorleucine, D-N-methylnorleucine, D-homoarginine, L-αN-methylhomoarginine, D-αN-methylhomoarginine, D-homolysine, L-α-N-methylhomolysine and L-αN-methylhomolysine.

In some embodiments the N-terminal amino acid residue is N-BzlGly which represents N-benzylglycine which has the structure:

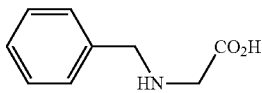

As used herein, the term "4-$R_3$-Phe" represents phenylalanine with a substituent in the 4-position of the phenyl ring:

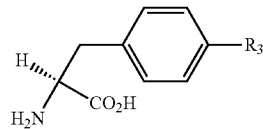

The substituent is an electron-withdrawing substituent. As used herein, the term "electron-withdrawing substituent" refers to a substituent which is more electronegative than the carbon atom to which it is attached and has a greater electron density. Examples of electron withdrawing substituents include fluorine (F), chlorine (Cl), bromine (Br), cyano (CN), nitro ($NO_2$), perfluoroalkyl groups such as $CF_3$, amines such as $NH_2$, NH(alkyl) and NH(alkyl)$_2$ and carbonyl containing substituents such as aldehydes (C(=O)H) and ketones (C(=O)alkyl). In some embodiments, where a one letter code for Phe (F) is used, 4-$R_3$-Phe may be represented by F(4$R_3$). For example, F(4F) is 4-fluorophenylalanine, where $R_3$ is fluorine and F(4-$NO_2$) is 4-nitrophenylalanine where $R_3$ is nitro.

The term "alkyl" refers to a linear or branched, saturated hydrocarbon chain having 1 to 20 carbon atoms. In some instances the number of carbon atoms is listed, for example, $C_{1-6}$ alkyl has 1, 2, 3, 4, 5 or 6 carbon atoms. Examples of suitable alkyl groups include, but are not limited to, methyl, ethyl, propyl, 1-methylethyl, butyl, 1,1-dimethylethyl, 1-methylpropyl, 2-methylpropyl, pentyl and hexyl.

As used herein, the term "cycloalkyl" refers to a cyclic hydrocarbon that may be saturated or unsaturated. The cycloalkyl ring may include a specified number of carbon atoms. For example, a 5 to 8 membered carbocyclic ring includes 5, 6, 7 or 8 carbon atoms. Examples of suitable cycloalkyl rings include, but are not limited to, cyclopentanyl, cyclopentenyl, cyclohexanyl, cyclohexenyl, cycloheptanyl, cycloheptenyl, cycloheptadienyl, cycloheptatrienyl, cyclooctanyl, cyclooctenyl, cyclooctadienyl and cyclooctatrienyl rings.

As used herein, the term "aryl" is intended to mean any stable, monocyclic or bicyclic carbon ring of up to 7 atoms in each ring, wherein at least one ring is aromatic. Examples of such aryl groups include, but are not limited to, phenyl, naphthyl, tetrahydronaphthyl, indanyl, biphenyl and binaphthyl.

The term "heterocyclic" as used herein, refers to a cyclic hydrocarbon in which one to four carbon atoms have been replaced by heteroatoms independently selected from N, S and O. A heterocyclic ring may be saturated or unsaturated. Examples of suitable heterocyclyl groups include tetrahydrofuranyl, tetrahydrothiophenyl, pyrrolidinyl, pyrrolinyl, pyranyl, piperidinyl, pyrazolinyl, dithiolyl, oxathiolyl, dioxanyl, dioxinyl and oxazinyl.

The term "heteroaryl" as used herein, represents a stable monocyclic or bicyclic ring of up to 7 atoms in each ring, wherein at least one ring is aromatic and at least one ring contains from 1 to 4 heteroatoms selected from the group consisting of O, N and S. Heteroaryl groups within the scope of this definition include, but are not limited to, acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline.

The term "basic amino acid residue" refers to an amino acid residue that has a positive charge at pH 7. Examples of basic amino acid residues include, but are not limited to, L-lysine, L-arginine, L-histidine, L-ornithine, L-αN-methyllysine, L-αN-methylarginine, L-αN-methylhistidine, L-3-methylhistidine, L-2,3-diaminopropionic acid, L-2,4-diaminobutanoic acid, L-homolysine and L-homoarginine, D-lysine, D-arginine, D-histidine, D-ornithine, D-αN-methyllysine, D-αN-methylarginine, D-αN-methylhistidine, D-3-methylhistidine, D-2,3-diaminopropionic acid, D-2,4-diaminopropionic acid, D-homolysine, D-homoarginine, L-αN-methylornithine, L-2N-methyl-2,3-diaminopropionic acid, L-2N-methyl-2,4-diaminobutanoic acid, L-αN-methylhomolysine, L-αN-methylhomoarginine, D-αN-methylornithine, D-2N-2,3-diaminopropionic acid, D-2N-2,4-diaminobutionic acid, D-αN-methylhomolysine and D-αN-methylhomoarginine, especially L-lysine, L-arginine, L-histidine, L-ornithine, L-αN-methyllysine, L-αN-methylarginine, L-αN-methylhistidine, L-3-methylhistidine, L-2,3-diaminopropionic acid, L-2,4-diaminobutanoic acid, L-homolysine and L-homoarginine.

As used herein, the term "N-terminal capping group" is a group that is covalently bonded to the N-terminus amino group and may in some cases mimic an amino acid side chain. Suitable N-terminal capping groups include acyl groups, for example, $CH_3CO$—, $CH_3CH_2CO$—, $CH_3CH_2CH_2CO$—, $CH_3(CH_2)_3CO$—, $CH_3(CH_2)_4CO$—, $CH_3(CH_2)_5CO$—, $CH_3(CH_2)_6CO$—, $CH_3(CH_2)_7CO$—, $CH_3(CH_2)_8CO$—, $CH_3(CH_2)_9CO$—, $CH_3(CH_2)_{10}CO$—, $CH_3(CH_2)_{11}CO$—, $CH_3$—$(CH_2)_4$(cis-$CH_2$=$CH_2$)$CH_2$(cis-CH=$CH_2$)$(CH_2)_7$—CO—, $CH_3(CH_2)_4$(cis-CH=CH)$CH_2$(cis-CH=CH)$CH_2$(cis-CH=CH)—$(CH_2)_4$—CO—, $CH_3(CH_2)_{12}$—CO— and $CH_3(CH_2)_{14}$—CO—. Other embodiments are where a capping group with an alcohol substituent, such as cholesterol, is attached to the N-terminus through a linker, such as a diacid linker, where one carboxylic acid group of the linker forms an amide bond with the N-terminus and the other carboxylic acid group forms an ester with an alcohol of the capping group. Suitable diacid linkers for attaching the hydroxyl containing capping group include

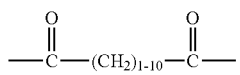

and

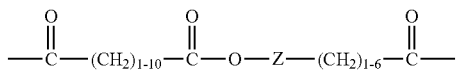

wherein Z is a cycloalkyl, aryl, heterocyclyl or heteroaryl group and wherein one or more —CH$_2$— groups may be replaced by a heteroatom selected from —O—, —S— and —N(R$_4$)— where R$_4$ is hydrogen or C$_1$-C$_6$ alkyl. In particular embodiments, the diacid linker is succinic acid, glutaric acid, adipic acid or a group

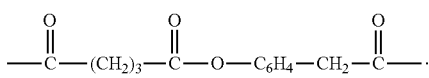

While any group with a hydroxyl substituent may act as a capping group with a linker, in particular embodiments the capping group is cholesterol. In yet other embodiments, the N-terminal capping group is a guanyl or substituted guanyl group, for example, CH$_3$NHC(=NH)—, H$_2$NC(=NCH$_3$)— and CH$_3$NHC(=NCH$_3$)—.

The term "C-terminal capping group" is a group that is covalently bonded to the C-terminal carboxy group or transforms the C-terminal carboxy group into an amide group. In some embodiments, the C-terminal capping group assists in stabilization of helical structure, for example, by participating in hydrogen bonds. Suitable C-terminal capping groups include amine and substituted amines. Examples of suitable amines include, but are not limited to, —NH$_2$, —NH(alkyl) such as —NH(methyl), —NH(ethyl), —NH(propyl), and —N(alkyl)$_2$ such as —N(methyl)$_2$, —N(ethyl)$_2$ and —N(methyl)(ethyl), especially —NH$_2$ and —NH(alkyl).

The nociceptin peptide mimetics of the invention include two 20 backbone atom macrocyclic rings which are separated by two amino acids, preferably Arg and Lys. The 20 atom macrocyclic rings are formed by cyclization of a lysine side chain amino group with an aspartic acid carboxy group to form a lactam bridge connecting amino acids five residues apart. The term "lactam bridge" refers to the formation of an amide bond —NH—C(=O)— that closes a ring to form a cyclic structure.

In some embodiments, the peptides of formula (I) are peptides of formula (II):

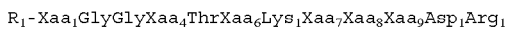

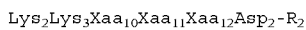

(II)

wherein
Xaa$_1$ is Phe or N-BzlGly;
Xaa$_4$ is Phe or 4-R$_3$Phe;
Xaa$_6$ is any amino acid residue, especially Gly, L-Ala, L-Glu, D-Ala, L-Arg and L-Pro, more especially Gly;
and R$_1$, R$_2$, R$_3$, Xaa$_7$, Xaa$_8$, Xaa$_9$, Xaa$_{10}$, Xaa$_{11}$ and Xaa$_{12}$ are as defined for formula (I).

In particular embodiments of peptides of formula (I) or formula (II), at least one of the following applies:
R$_1$ is H;
R$_2$ is —OH, —NH$_2$ or —NH(alkyl), especially —OH, —NH$_2$ or —NH(CH$_3$);
Xaa$_1$ is L-Phe or N-BzlGly;
Xaa$_2$ is Gly;
Xaa$_3$ is Gly;
Xaa$_4$ is L-Phe or 4-R$_3$-Phe;
Xaa$_5$ is L-Thr or L-Ser, especially L-Thr;
Xaa$_6$ is selected from Gly, L-Ala, L-Ser, L-Lys, L-Arg, L-Pro, L-Glu, L-Ile, L-Met, D-Ala, D-Ser, D-Lys, D-Arg, D-Pro, D-Glu, D-Ile, D-Leu, D-Met and D-Val, more especially Gly, L-Lys, L-Ala, D-Ala, L-Arg and L-Glu, most especially Gly or L-Lys;
Xaa$_7$ is selected from L-Arg, L-Lys, L-Orn, L-Ala, L-Leu, L-Met, L-Glu, L-Gln, L-Cys, L-Val, L-Ile, L-Phe, L-Tyr, L-Trp, L-Thr, Gly, L-Ser and L-Asp, especially L-Arg and L-Lys, more especially L-Arg;
Xaa$_8$ is selected from L-Lys, L-Orn, L-Arg, L-His, L-2,3-diaminopropionic acid and L-2,4-diaminobutanoic acid, especially L-Lys and L-Orn, more especially L-Lys;
Xaa$_9$ is selected from L-Ser, D-Ser, L-Thr, L-Cys, L-Asn, L-Gln, L-Tyr, L-Ala, L-Val, L-Leu, L-Ile, L-Met, L-Phe, L-Trp, L-Pro, L-Arg and Gly, especially L-Ser, D-Ser, L-Ala, L-Leu, L-Met, L-Gln, L-Pro, L-Arg and L-Phe, most especially L-Ser;
Xaa$_{10}$ is selected from L-Ala, L-Lys, L-Arg, L-Orn, L-Leu, L-Ile, L-Val, L-Met, L-Phe, L-Trp, Gly, L-Ser, L-Thr, L-Cys, L-Gln, L-Asn, L-Tyr and L-His, especially L-Ala, L-Lys, L-Orn, L-Arg, L-Asn, L-Glu, L-Leu, L-Met, L-Gln and L-Phe, more especially L-Ala, L-Leu, L-Lys, L-Arg and L-Asn;
Xaa$_{11}$ is selected from L-Asn, L-Ser, L-Thr, L-Cys, L-Gln, L-Tyr, L-Ala, L-Val, L-Leu, L-Ile, L-Met, L-Phe, L-Trp and Gly, especially L-Asn, L-Ala, L-Leu, L-Met, L-Gln and L-Phe, more especially L-Asn, L-Gln and L-Ala;
Xaa$_{12}$ is selected from L-Gln, L-Asn, L-Arg, L-Lys, L-Ser, L-Thr, L-Cys, L-Tyr, L-Ala, L-Val, L-Leu, L-Ile, L-Met, L-Phe, L-Trp and Gly, especially L-Gln, L-Asn, L-Arg, L-Lys, L-Ala, L-Leu, L-Met and L-Phe, more especially L-Gln, L-Asn, L-Arg and L-Lys;
R$_3$ is selected from —F, —Cl, —Br, —I, —CN, —CF$_3$, —NH$_2$, —N(CH$_3$)$_2$, —NO$_2$, —CHO and —COalkyl, especially —F, —Cl, —Br, —I, —CN, —CF$_3$ and NO$_2$, more especially —F and —NO$_2$.

In some embodiments, the peptide of formula (I) are agonist of ORL-1 and are peptides of formula (III):

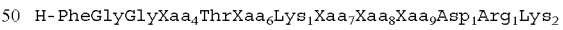

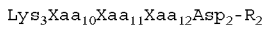

(III)

wherein Xaa$_4$, Xaa$_6$, Xaa$_7$, Xaa$_8$, Xaa$_9$, Xaa$_{10}$, Xaa$_{11}$, Xaa$_{12}$ and R$_2$ are as defined in formula (I).

In particular embodiments of formula (III) one or more of the following apply:
Xaa$_4$ is L-Phe or L-4-R$_3$-Phe;
Xaa$_6$ is a naturally-occurring amino acid, especially Gly, L-Ala L-Ile, L-Leu, L-Met or L-Val, more especially Gly;
Xaa$_7$ is selected from a basic amino acid residue, L-Ala, L-Leu, L-Met, L-Glu, L-Gln, L-Cys, L-Val, L-Ile, L-Phe, L-Tyr, L-Trp, L-Thr, Gly, L-Ser and L-Asp, especially L-Arg, L-Lys, L-Orn, L-Ala, L-Leu, L-Met, L-Glu, L-Gln, L-His, L-Cys, L-Val and L-Ile, more especially L-Arg and L-Lys, most especially. L-Arg;

Xaa₈ is selected from L-Lys, L-Orn, L-Arg, L-His, L-2,3-diaminopropionic acid and L-2,4-diaminobutanoic acid, especially L-Lys and L-Orn, more especially L-Lys;

Xaa₉ is selected from L-Ser, D-Ser, L-Thr, L-Cys, L-Asn, L-Gln, L-Tyr, L-Ala, L-Val, L-Leu, L-Ile, L-Met, L-Phe, L-Trp, L-Pro, L-Arg and Gly, especially L-Ser, L-Ala, L-Leu, L-Met, L-Gln and L-Phe, most especially L-Ser;

Xaa₁₀ is selected from L-Ala, L-Leu, L-Ile, L-Val, L-Met, L-Phe, L-Trp, L-Gly, L-Ser, L-Thr, L-Cys, L-Gln, L-Asn, L-Tyr and His, especially L-Ala, L-Lys, L-Orn, L-Arg, L-Asn, L-Glu, L-Leu, L-Met, L-Gln and L-Phe, most especially L-Ala, L-Lys and L-Asn;

Xaa₁₁ is selected from L-Asn, L-Ser, L-Thr, L-Cys, L-Gln, L-Tyr, L-Ala, L-Val, L-Leu, L-Ile, L-Met, L-Phe, L-Trp and L-Gly, especially L-Asn, L-Ala, L-Leu, L-Met, L-Gln and L-Phe, most especially L-Asn, L-Gln and L-Ala;

Xaa₁₂ is selected from L-Gln, L-Asn, L-Arg, L-Lys, L-Ser, L-Thr, L-Cys, L-Tyr, L-Ala, L-Val, L-Leu, L-Ile, L-Met, L-Phe, L-Trp and Gly, especially L-Gln, L-Asn, L-Arg, L-Lys, L-Ala, L-Leu, L-Met and L-Phe, most especially L-Gln and L-Asn;

R₃ is selected from —F, —Cl, —Br, —I, —CN, —CF₃, —NH₂, —N(CH₃)₂, —NO₂, —CHO, —COalkyl, especially where R₃ is —F, —Cl, —Br, —I, —CN, —CF₃ and —NO₂, more especially —F and —NO₂.

Particular agonist peptides include:

```
                                      SEQ ID NO: 7
H-FGGFTG[KRKSD]RK[KANQD]-NH₂

SEQ ID NO: 8
H-FGGF(4F)TG[KRKSD]RK[KKNQD]-NH₂

SEQ ID NO: 17
H-FGGFTG[KRKSD]RK[KANQD]-OH

SEQ ID NO: 18
H-FGGFTG[KRKSD]RK[KKNQD]-OH
``` where the square brackets indicate the formation of a lactam bridge between the lysine (K) side chain amino group and the aspartic acid (D) side chain carboxy group thereby forming a macrocycle.

In a particular embodiment, the peptides of formula (I) are antagonists of ORL-1 and are peptides of formula (IV)

```
R₁-Xaa1Xaa₂Xaa₃Xaa₄Xaa₅Xaa₆Lys₁Xaa₇Xaa₈Xaa₉Asp₁

Arg₁Lys₂Lys₃Xaa₁₀Xaa₁₁Xaa₁₂Asp₂-R₂

(IV)
``` wherein
Xaa₁ is N-BzlGly;
and Xaa₂, Xaa₃, Xaa₄, Xaa₅, Xaa₆, Xaa₇, Xaa₈, Xaa₉, Xaa₁₀, Xaa₁₁, Xaa₁₂ R₁ and R₂ are as defined for formula (I).

In particular embodiments, one or more of the following apply:
Xaa₁ is N-BzlGly;
Xaa₂ is Gly;
Xaa₃ is Gly;
Xaa₄ is L-Phe or L-4-R₃-Phe;
Xaa₅ is L-Thr or L-Ser, especially L-Thr;
Xaa₆ is a naturally-occurring amino acid, especially Gly, L-Ala, L-Ser, L-Lys, L-Pro, L-Arg, L-Glu, L-Ile, L-Leu, L-Met, L-Val, D-Ser, D-Lys, D-Arg, D-Pro, D-Glu, D-Ile, D-Leu, D-Met or D-Val, more especially Gly, L-Lys, L-Ala, D-Ala, L-Arg and L-Glu, most especially Gly or L-Lys;
Xaa₇ is selected from a basic amino acid residue, L-Ala, L-Leu, L-Met, L-Glu, L-Gln, L-Cys, L-Val, L-Ile, L-Phe, L-Tyr, L-Trp, L-Thr, L-Gly, L-Ser and L-Asp, especially L-Arg, L-Lys, L-Orn, L-Ala, L-Leu, L-Met, L-Glu, L-Gln, L-His, L-Cys, L-Val and L-Ile, more especially L-Arg and L-Lys, most especially L-Arg;

Xaa₈ is selected from L-Lys, L-Orn, L-Arg, L-His, L-2,3-diaminopropionic acid and L-2,4-diaminobutanoic acid, especially L-Lys and L-Orn, more especially L-Lys;

Xaa₉ is selected from L-Ser, D-Ser, L-Thr, L-Cys, L-Asn, L-Gln, L-Tyr, L-Ala, L-Val, L-Leu, L-Ile, L-Met, L-Phe, L-Trp, L-Pro, L-Arg and Gly, especially L-Ser, L-Ala, L-Leu, L-Met, L-Gln, L-Pro, L-Arg and L-Phe, most especially L-Ser;

Xaa₁₀ is selected from L-Ala, L-Leu, L-Ile, L-Val, L-Met, L-Phe, L-Trp, L-Gly, L-Ser, L-Thr, L-Cys, L-Gln, L-Asn, L-Tyr, L-Lys, L-Orn, L-His and L-Arg, L-especially L-Ala, L-Lys, L-Orn, L-Arg, L-Asn, L-Glu, L-Leu, L-Met, L-Gln and L-Phe, most especially L-Ala, L-Lys, L-Arg and L-Asn;

Xaa₁₁ is selected from L-Asn, L-Ser, L-Thr, L-Cys, L-Gln, L-Tyr, L-Ala, L-Val, L-Leu, L-Ile, L-Met, L-Phe, L-Trp and L-Gly, especially L-Asn, L-Ala, L-Leu, L-Met, L-Gln and L-Phe, most especially L-Asn, L-Gln and L-Ala;

Xaa₁₂ is selected from L-Gln, L-Asn, L-Arg, L-Lys, L-Ser; L-Thr, L-Cys, L-Tyr, L-Ala, L-Val, L-Leu, L-Ile, L-Met, L-Phe, L-Trp and Gly, especially L-Gln, L-Asn, L-Arg, L-Lys, L-Ala, L-Leu, L-Met and L-Phe, most especially L-Gln, L-Asn, L-Arg and L-Leu;

R₃ is selected from —F, —Cl, —Br, —I, —CN, —CF₃, —NH₂, —N(CH₃)₂, —NO₂, —CHO, —COalkyl, especially where R₃ is selected from —F, —Cl, —Br, —I, —CN, —CF₃ and —NO₂, more especially —F and —NO₂.

Particular antagonist peptides include:

```
                                      SEQ ID NO: 12
BzlGlyGGFTG[KRKSD]RK[KKNQD]-NH₂

SEQ ID NO: 13
BzlGlyGGF(4F)TG[KRKSD]RK[KKNQD]-NH₂

SEQ ID NO: 19
BzlGlyGGFTG[KRKSD]RK[KKNQD]-OH

SEQ ID NO: 20
BzlGlyGGF(4F)TG[KRKSD]RK[KKNQD]-OH
``` where the square brackets indicate the formation of a lactam bridge between the lysine (K) side chain amino group and the aspartic acid (D) side chain carboxy group thereby forming a macrocycle.

The peptides of the present invention may be prepared by methods of synthesis known in the art, such as solution phase or solid phase synthesis, especially solid phase synthesis (Kates and Albericio (2000), Solid Phase Synthesis: a practical guide; eds Kates & Albericio (Marcel Dekker, NY)]

In particular embodiments, the peptides are prepared by solid phase peptide synthesis which is performed using Fmoc chemistry using O-Benzothiazole-N,N,N',N'-tetramethyluronium-hexafluorophosphate (HTBU) or 2-(1H-7-azabenzotriazol-1-yl)-1,1,3,3-tetramethyl uronium hexafluorophosphate methanaminium (HATU)/diisopropylethylamine (DIPEA) activation and Fmoc deprotection with dimethylformamide (DMF)/piperidine. Other reagents for activation and deprotection are known in the art and are also suitable for use in the present synthesis. For example, other coupling reagents for activation of carboxy groups include N—N'-carbonyldiimidazole (CDI), N,N'-dicyclohexylcarbodiimide (DCC), benzyotriazole-1-yl-oxy-tris-(dimethylamino)-phosphonium hexafluorophosphate (BOP), 3-(Diethoxy-phosphoryloxy)-3H-benzo[d][1,2,3]-triazin-4-one (DEPBT), N,N'-diisopropylcarbodiimide (DIC), 1-ethyl-3-(3- dimethylaminopropyl)carbodiimide hydrochloride (EDC HCL), 1-hydroxy-7-azabenzotriazole (HOAt), N-hydroxybenzotriazole (HOBT), hydroxy-3,4-dihydro-4-oxo-1,2,3-benzotriazine (HOOBT), 1H-benzotriazolium-1-[bis(dimethylamino)methylene]-5-chloro-hexafluorophosphate-3-oxide (HCTU), 6-chloro-1-hydroxybenzotriazole (Cl-HOBt), benzotriazol-1-yl-oxytripyrrolidinophosphonium hexafluorophosphate (PyBOP), bromo-tris-pyrrolidinophosphonium hexafluorophosphate (PyBrOP), O-(benzotriazol-1-yl)-N,N,N',N'-tetramethyluronium tetrafluoroborate (TBTU), N,N,N',N'-tetramethyl-O-(3,4-dihydro-4-oxo-benzotriazin-3-yl)uronium tetrafluoroborate (TDBTU), 2-(7-aza-1H-benzotriazol-1-yl)-1,1,3,3-tetramethyluronium tetrafluoroborate (TATU), O—(N-succinimidyl)-1,1,3,3-tetramethyluronium tetrafluoroborate (TSTU) and 4,5-dicyanoimidazole.

The peptides are synthesized by addition of appropriately protected amino acids to a solid phase resin in a stepwise manner. The entire peptide may be synthesized before cyclization of the lysine and aspartic acid side chains to form the bicyclic peptide.

Alternatively, cyclization may occur during peptide synthesis in a stepwise manner. For example, the amino acids for the C-terminus of the peptide may be assembled until all the amino acids for the macrocyclic ring near the C-terminus are present. Immediately after addition of the $Lys_3$ residue, $Asp_2$ and $Lys_3$ side chains are deprotected and cyclized to form the lactam bridge of the macrocycle. The next amino acids are then added to the peptide until the amino acids for the macrocycle near the N-terminus are present. The $Asp_1$ and $Lys_1$ side chains are then deprotected and cyclized to form the lactam bridge of the second macrocycle. Any further amino acid residues required are then added to the N-terminus of the peptide before cleavage from the resin and/or deprotection of the N-terminus and side chain protecting groups. In particular embodiments, stepwise assembly of the macrocyclic rings occurs.

Any suitable lysine and aspartic acid side chain protecting groups can be used provided they can be removed without removing side chain protecting groups of other residues including $Lys_2$. A person skilled in the art would be able to determine suitable protecting group strategies. Reactive groups on the side chains, including the lactam bridge forming substituents are suitably protected, for example, carboxy groups can be suitably protected as esters such as methyl, ethyl, allyl, benzyl, t-butyl, phenyl or phenylisopropyl esters and amino groups can be suitably protected with alkyloxy carbonyl, allyloxycarbonyl (Alloc), benzyloxycarbonyl (Z), t-butoxycarbonyl (Boc), 2-(4-biphenylyl)-isopropoxycarbonyl (Bpoc), 9-fluorenylmethoxycarbonyl (Fmoc), triphenylmethyl (trityl), N-methyltrityl (Mtt) or 2-nitrophenylsulphenyl (Nps) groups, which may be removed after synthesis of the peptide and before reaction to form the lactam bond linkage. Suitable methods for selectively protecting and deprotecting functional groups can be found in Green & Wutz, Protective Groups in Organic Synthesis, 3$^{rd}$ Edition, John Wiley & Sons, 1999, and Taylor (2002), Biopolymers, 66:49. In one particular embodiment, $Lys_1$ and $Lys_3$ side chains are protected with N-methyltrityl (Mtt) groups and $Asp_1$ and $Asp_2$ are protected as the phenylisopropyl ester (OPIP), both of which may be readily removed with 3% trifluoroacetic acid (TFA) in dichloromethane (DCM). The protecting groups on other side chains can be selected such that they are not removed under these conditions.

Amide formation to prepare the lactam-bridged macrocycles can be achieved by methods known in the art including activation of the aspartic acid side chain carboxy group by, for example, formation of an acid chloride, acid anhydride, an acylazide, a carbodiimide, an acyloxyposphonium, or uronium compound or active ester, which is susceptible to nucleophilic attack from the amine nitrogen atom of the lysine side chain amino group. For example, activating coupling agents described above for peptide amide bond formation may be used to form the amide bond of the lactam bridge. In a particular embodiment, the method of activating the side chain carboxylic acid of the aspartic acid residue to nucleophilic attack is preparation of an acyloxyphosphonium or uronium derivative of the carboxylic acid, for example, by reaction of the carboxylic acid with benzotriazolyloxy-tri-(dimethylamino)phosphonium hexafluorophosphate (BOP) or benzotriazolyloxy-tris-(pyrrolidinyl)phosphonium hexafluorophosphate (Py-BOP) in the presence of a tertiary amine such as triethylamine or diisopropylethylamine (DIPEA) or similar reaction using Benzotriazol-1-yl-1,1,3,3-tetramethyluronium ion (HBTU). In one particular embodiment, the aspartic acid side chain carboxylic acid is activated by BOP in the presence of DIPEA to form the lactam amide bond.

The peptides, once synthesized and cyclized can be removed from the solid phase synthesis resin by methods known in the art. The method used will depend on the resin used and a person skilled in the art could readily determine suitable cleavage conditions. For example, when Rink-Amide-MBHA-LL-resin is used, cleavage may be achieved with 95% TFA and 2.5% tri-isopropylsilane (TIPS) in water.

The peptides of the invention are suitable for treating or preventing diseases or disorders ameliorated by modulation of the ORL-1 receptor. Examples of diseases and disorders ameliorated by modulation of the ORL-1 receptor include anxiety and mood, depression, panic, mania, dementia, bipolar disorder, substance abuse, neuropathic pain, peripheral pain, acute pain, chronic pain, migraine, asthma, neuronal function disorders, cough, psychosis, schizophrenia, convulsive disorders such as epilepsy, hypertension, water retention, obesity, metabolic syndrome including type 2 diabetes, hypotension, eating disorders such as anorexia nervosa, bulimia and binge eating, cravings, diabetes, cardiac arrhythmia, cardiac edema, heart failure, cardiovascular disorders including cardiac fibrosis, gastrointestinal disorders, irritable bowel syndrome, Crohn's disease, urinary incontinence, adrenal disorders such as Addison's disease and Cushing's syndrome, attention deficit disorder (ADD), attention deficit hyperactivity disorder (ADHD), motor function and locomotion disorders, learning disorders, neurodegenerative disorders such as Alzheimer's disease and Parkinson's disease, adult respiratory distress syndrome (ARDS), bradycardia, stroke, impotency, respiratory disorders and altered pulmonary function such as obstructive pulmonary disease. The peptides of formula (I) may also be useful for improving cognition or memory, for mood stabilization, and for preventing development of tolerance to opiates such as morphine.

Diseases for which agonists may be useful include, but are not limited to, neuropathic pain, migraine, anxiety, anorexia, diuresis, spatial memory disorders, drug addiction (alcohol, morphine, cocaine, amphetamine), urinary incontinence, cough and other respiratory disorders, asthma, sepsis, cardiac edema, hypertension, impotency, stroke, seizures and chronic pain conditions.

Diseases for which antagonists may be useful include, but are not limited to, depression, dementia, Parkinson's disease and neurodegenerative diseases such as Alzheimer's disease. Antagonists may also provide general analgesia.

The peptides of the invention are administered in an effective amount. As used herein, the term "effective amount"

relates to an amount of compound which, when administered according to a desired dosing regimen, provides the desired mediation of the disease or disorder, therapeutic activity or disease prevention. Dosing may occur at intervals of minutes, hours, days, weeks, months or years or continuously over any one of these periods. A therapeutic or treatment effective amount is an amount of the compound which, when administered according to a desired dosing regimen, is sufficient to at least partially attain the desired therapeutic effect, or delay the onset of, or inhibit the progression of or halt or partially or fully reverse the onset or progression of the disease or disorder. A prevention effective amount of compound which when administered to the desired dosing regimen is sufficient to at least partially prevent or delay the onset of a particular disease or condition.

Suitable dosages may lie within the range of about 0.01 ng per kg of body weight to 1 g per kg of body weight per dosage. The dosage is suitably in the range of 1 ng to 1 g per kg of body weight per dosage, such as is in the range of 1 µg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage.

Suitable dosage amounts and dosing regimens can be determined by the attending physician and may depend on the severity of the condition as well as the general age, health and weight of the subject.

The active ingredient may be administered in a single dose or a series of doses. While it is possible for the active ingredient to be administered alone, it is preferable to present it as a composition, for example, a pharmaceutical composition.

According to a further aspect, the invention contemplates a pharmaceutical composition comprising a peptide of the invention or a pharmaceutically acceptable salt thereof and a pharmaceutically acceptable carrier, excipient or diluent.

Suitable pharmaceutically acceptable salts include, but are not limited to, salts of pharmaceutically acceptable inorganic acids such as hydrochloric, sulfuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine.

Basic nitrogen-containing groups may be quaternised with such agents as lower alkyl halide, such as methyl, ethyl, propyl, and butyl chlorides, bromides and iodides; dialkyl sulfates like dimethyl and diethyl sulfate; and others.

The formulation of such compositions is well known to those skilled in the art. The composition may contain pharmaceutically acceptable additives such as carriers, diluents or excipients. These include, where appropriate, all conventional solvents, dispersion agents, fillers, solid carriers, coating agents, antifungal and antibacterial agents, dermal penetration agents, surfactants, isotonic and absorption agents and the like. It will be understood that the compositions of the invention may also include other supplementary physiologically active agents.

The carrier must be pharmaceutically acceptable in the sense of being compatible with the other ingredients of the composition and not injurious to the subject. Compositions include those suitable for oral, rectal, inhalational, nasal, transdermal, topical (including buccal and sublingual), vaginal or parenteral (including subcutaneous, intramuscular, intraspinal, intravenous and intradermal) administration. The compositions may conveniently be presented in unit dosage form and may be prepared by any methods well known in the art of pharmacy. Such methods include the step of bringing, into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste. A tablet may be made by compression or moulding, optionally with one or more accessory ingredients. Compressed tablets may be prepared by compressing in a suitable machine the active ingredient in a free-flowing form such as a powder or granules, optionally mixed with a binder (eg inert diluent, preservative, disintegrant (eg. sodium starch glycolate, cross-linked polyvinyl pyrrolidone, cross-linked sodium carboxymethyl cellulose)) surface-active or dispersing agent. Moulded tablets may be made by moulding in a suitable machine a mixture of the powdered peptide moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavored base, usually sucrose and acacia or tragacanth gum; pastille's comprising the active ingredient in an inert basis such as gelatin and glycerin, or sucrose and acacia gum; and mouthwashes comprising the active ingredient in a suitable liquid carrier.

The peptides of the invention may also be administered intranasally or via inhalation, for example by atomizer, aerosol or nebulizer means.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal devices, such as patches, may also be used to administer the compounds of the invention.

Compositions for rectal administration may be presented as a suppository with a suitable carrier base comprising, for example, cocoa butter, gelatin, glycerin or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate, fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavoring agents, disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavoring agents include peppermint oil, oil of wintergreen, cherry, orange or raspberry flavoring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The peptides of the invention may be usefully combined with another pharmacologically active compound, or with two or more other pharmacologically active compounds either for use in the method of the invention or in a composition of the invention. For example, an ORL-1 receptor agonist or antagonist, particularly a peptide of formula (I), or a pharmaceutically acceptable salt or solvate thereof, as defined above, may be administered in a single composition or simultaneously, sequentially and separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobarbital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquino-1-2-yl)-5-(2-pyridyl)quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. ((αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6,13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular, paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a 5-HT$_1$B/1D agonist such as eletriptan, sumatriptan, naratriptan, zolmitriptan or rizatriptan;

a 5-HT$_2$A receptor antagonist such as R(+)-alpha-(2,3-dimethoxy-phenyl)-1-[2-(4-fluorophenylethyl)]-4-piperidinemethanol (M DL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-prop-yl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-di-hydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydromethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

a cannabinoid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,I-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S, 4R)-2-amino-4-[[2-chloro-5-(trifluormethyl)phenyl]thio]-5-thiazolebutanol, 2-[[(1R,3S)-3-amino-4-hydroxy-1-(5-thiazolyl)butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl]benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxymethyl]-1-methyl-2-quinolone (ZD-2138), or 2,3,5-trimethyl-6-(3-pyridylmethyl)-1,4-benzoquinone (CV-6504);

a sodium channel blocker, such as lidocaine;

a 5-HT3 antagonist, such as ondansetron;

stimulant drugs such as Ritilin, Concerta or non-stimulants such as Straterra;

amphetamines such as dexedrine or adderall;

and the pharmaceutically acceptable salts and solvates thereof.

In another aspect of the invention there is provided a use of a peptide of formula (I) as described above or a pharmaceutically acceptable salt thereof in the manufacture of a medicament for the treatment or prevention of diseases or disorders ameliorated by modulation of the ORL-1 receptor.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The invention will now be described with reference to the following examples which are included for the purpose of illustration only and are not intended to limit the generality of the invention hereinbefore described.

EXAMPLES

Example 1

Peptide Synthesis

Figure 1:
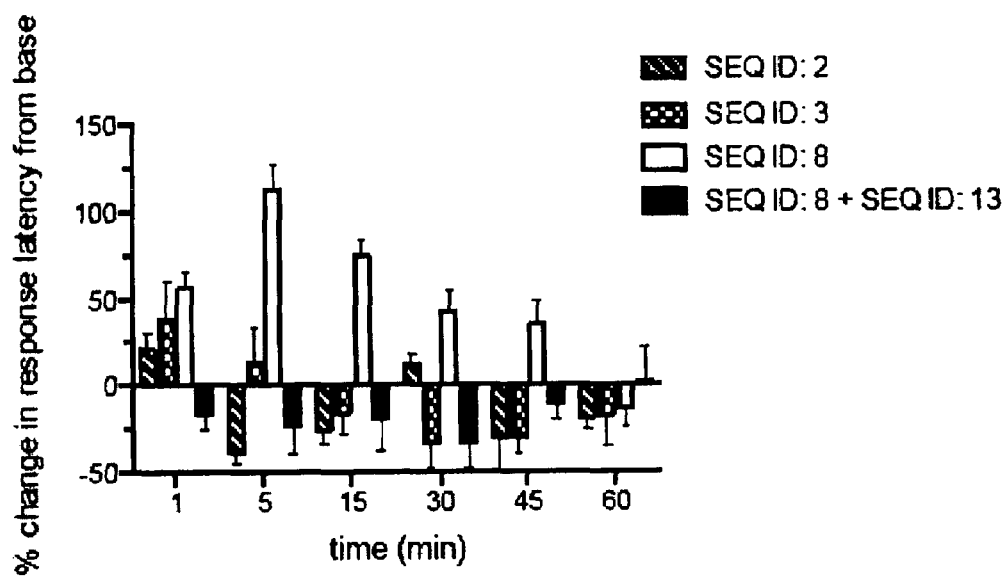
FIG. 1 is a graphical representation showing the nociceptive activity of ORL-1 agonist (SEQ ID NO:8) in C57BL/6 mice as front paw withdrawal latency on a hot plate (53° C.) after various times in comparison to unconstrained peptides SEQ ID NO:2 and SEQ ID NO:3 and when co-administered with SEQ ID NO:13.

Nociceptin analogues were prepared on 0.15 mmol scale by manual stepwise solid phase peptide synthesis using HBTU/DIPEA activation for Fmoc chemistry [Kates and Albericio, 2000, Solid-Phase Synthesis: A Practical Guide, Eds: Kates and Albericio, Marcel Dekker, NY] on Rink Amide MBHA LL resin (substitution 0.37 mmol·$g^{-1}$). Fmoc deprotections were achieved with 2×5 min treatments with DMF/Piperidine (1:1). Four equivalents of amino acid and four equivalents of diisopropylethylamine (DIPEA) were employed in each coupling step (15 min), except for Fmoc-Asp(OPip)-OH and Fmoc-Lys(Mtt)-OH where only 2 equivalents were coupled using HATU and DIPEA activation. Coupling yields were monitored by quantitative ninhydrin assay [Kaiser et al., 1970, Anal. Biochem. 34:595-598] and double couplings were employed for yields below 99.6%. After the first Fmoc-Lys(Mtt)-OH residue was coupled, the phenylisopropyl ester of aspartic acid and methyltrityl group of lysine were removed by treating the peptide resin with 3% TFA DCM (5×2 min), after which the ninhydrin test gave an intense blue, opaque solution. Cyclization was effected on-resin using 2.5 equiv. BOP, 2.5 equiv. DIPEA in DMF 0.5 M. The reaction was monitored by the ninhydrin test and MS after small cleavage with TFA. The same procedure was repeated to generate the second cycle. The peptide resin was then washed with DMF, MeOH/DCM and DCM, dried under nitrogen with suction for 1 hour. Peptides were cleaved by using 95% TFA, 2.5% TIPS, 2.5% $H_2O$ (6 mL) for 2 hours. The resin was then filtered off and the solvent evaporated under a stream of nitrogen. The peptides were precipitated with cold diethyl ether. The ether was decanted to give white solids which were re-dissolved in 1:1 acetonitrile/water and lyophilized. Crude peptides were purified by reverse-phase HPLC on Waters 486 system equipped with a Rheodyne semi-preparative injector with a 5 mL loop volume on a Phenomenex Luna C18 15 μm column, 250 mm×22 mm, at 20 mL/min using linear gradient elution 100% A to 55% A over 40 min (solvent A is water and 0.1% TFA; solvent B is 90% MeCN, 10% water, and 0.1% TFA) and UV detection at 214 nm. Purity of compounds assessed via analytical rpHPLC (Waters 996 (A) on a Phenomenex Luna C18 5 μm column, 250×4.60 mm, at 1 mL/min using a equilibrate 100% A for 10 min, then a linear gradient over 20 min and finally, 100% B for 10 min and with; or Agilent Technologies 1200 Series (B) under the same conditions that in Waters 996, but using an equilibrate time 100% A for 3 min previous to start the linear gradient, which affords changes in the retention times), mass spectrometry and NMR. The molecular weight of the peptide was determined by electrospray mass spectrometry on a Micromass LCT mass spectrometer. $^1$H NMR and 2D spectra were recorded on samples containing 1-5 mg peptide in $H_2O$/$D_2O$ (90:10) on Bruker Avance 600 spectrometer.

Reverse Phase HPLC retention times and mass spectrometry data of some representative peptide analogues are given in Table 4.

TABLE 4 rpHPLC retention times and mass spectrometry data of nociceptin peptide analogues.

| SEQ ID NO: | Sequence | RT (min) | $[M + XH]^{X+}$ Obs. x = 2 | x = 3 | x = 4 | Calc. |
|---|---|---|---|---|---|---|
| 1 | H-FGGFTGARKSARKLANQ-OH | 8.9[b] | 905.16 | 603.76 | | 1808.99 |
| 2 | H-FGGFTGARKSARKLANQ-$NH_2$ | 11.4[a] | 904.28 | 603.15 | 452.55 | 1806.80 |
| 3 | H-FGGF(4-F)TGARKSARKLKNQ-$NH_2$ | 9.0[a] | | 628.62 | 471.74 | 1880.90 |
| 4 | H-FGGFTGK(Ac)RKSNRKK(Ac)ANQN-$NH_2$ | 14.0[a] | 1061.24 | 707.76 | | 2121.14 |
| 5 | H-FGGFTGARKSARKAANQA-$NH_2$ | 14.6[a] | 919.17 | 613.07 | | 1838.05 |
| 6 | H-FGGFT[KARKD][KRKLD]-$NH_2$ | 15.1[a] | 865.70 | 577.43 | | 1730.0 |
| 7 | H-FGGFTG[KRKSD]RK[KANQD]-$NH_2$ | 13.8[a] | 1002.22 | 668.57 | | 2003.7 |
| 8 | H-FGGF(4-F)TG[KRKSD]RK[KKNQD]-$NH_2$ | 14.0[a] | 1040.10 | 693.71 | 520.60 | 2078.12 |
| 9 | BzlGGGFTGARKSARKLKNQ-$NH_2$ | 11.4[a] | 933.15 | 621.21 | | 1862.90 |
| 10 | BzlGGGF(4-F)TGARKSARKLKNQ-$NH_2$ | 8.7[b] | 942.76 | 628.50 | | 1880.90 |
| 11 | BzlGGGFTGARKSARK-$NH_2$ | 14.2[a] | 691.47 | 461.33 | | 1381.78 |
| 12 | BzlGGGFTG[KRKSD]RK[KKNQD]-$NH_2$ | 9.0[b] | 1030.11 | 687.25 | 515.63 | 2060.13 |
| 13 | BzlGGGF(4-F)TG[KRKSD]RK[KKNQD]-$NH_2$ | 13.9[a] | 1039.56 | 693.75 | 520.56 | 2078.12 |
| 14 | BzlGGGFT[KARKD[KRKLD]-$NH_2$ | 15.2[a] | 865.61 | 577.44 | | 1730.00 |

TABLE 4-continued rpHPLC retention times and mass spectrometry data of nociceptin peptide analogues.

| SEQ ID NO: | Sequence | RT (min) | [M + XH]^{X+} Obs. x = 2 | x = 3 | x = 4 | Calc. |
|---|---|---|---|---|---|---|
| 15 | Ac-[KRKSD]RK[KKNQD]-NH$_2$ | 13.2[a] | 768.21 | 512.44 | | 1535.89 |
| 16 | H-TG[KRKSD]RK[KKNQD]-NH$_2$ | 10.28[a] | 826.19 | 551.18 | | 1650.80 |

[a]Peptides purified under condition A. [b]Peptides purified under condition B.

Example 2

NMR Spectroscopy

The sample for NMR analysis of SEQ ID NOs:6 and 7 were prepared by dissolving the peptide (2.0-5.0 mg) in 540 μL H$_2$O and 60 μL D$_2$O. 1D and 2D $^1$H-NMR spectra were recorded on a Bruker Avarice DRX-600 spectrometer. 2D $^1$H-spectra were recorded in phase-sensitive mode using time-proportional phase incrementation for quadrature detection in the t1 dimension. [Marion, Wüthrich, 1983, Biochem. Biophys. Res. Commun., 113:967-974] The 2D experiments included TOCSY (standard Bruker mlevgpph pulse program) and NOESY (standard Bruker noesygpph pulse program) and dqfCOSY (standard Bruker dqfcosygpph pulse program). TOCSY spectra were acquired over 6887 Hz with 4096 complex data points in F2, 256 increments in F1 and 16 scans per increment. NOESY spectra were acquired over 6887 Hz with 4096 complex data points in F2, 512 increments in F1 and 32 scans per increment. TOCSY and NOESY spectra were acquired with several isotropic mixing times of 80 ms for TOCSY and 350 ms for NOESY. For all water suppression was achieved using modified WATERGATE NMR experiments, [Piotto, et al., *J. Biomol. NMR*, 2:661-665] and excitation sculpting sequence. For 1D $^1$H NMR spectra acquired in H$_2$O/D$_2$O (9:1), the water resonance was suppressed by low power irradiation during the relaxation delay (1.5 to 3.0 s). Spectra were processed using Topspin (Bruker, Germany) software and NOE intensities were collected manually. The t1 dimensions of all 2D spectra were zero-filled to 1024 real data points with 90° phase-shifted QSINE bell window functions applied in both dimensions followed by Fourier transformation and fifth order polynomial baseline correction. $^1$H chemical shifts were referenced to DSS (δ 0.00 ppm) in water. $^3J_{NHCHα}$ coupling constants were measured from 1D $^1$H NMR and dqf-COSY spectra.

$^1$H NMR assignments and chemical shifts for SEQ ID NO:6 are given in Table 5, for SEQ ID NO:7 in Table 6 and for SEQ ID NO:8 in Table 7.

TABLE 5

$^1$H NMR resonance assignments and chemical shifts (δ ppm) for SEQ ID NO: 6 in 90% H$_2$O:10% D$_2$O (298K).

| Residue F1 | NH | Hα | Hβ | Others |
|---|---|---|---|---|
| G2 | 8.53 | 3.81 | | |
| G3 | 7.88 | 3.77 | | |
| F4 | 8.29 | 4.57 | β1 2.97, β2 2.31 | δ1 7.17, δ2 7.17, ε1 7.27, ε2 7.27, Z - nd |
| T5 | 7.85 | 4.27 | 4.04 | γ 1.17 |
| K6 | 8.17 | 4.01 | 1.69 | NH 8.04, ε 3.58, γ1 1.44, γ2 1.08, δ 2.47 |
| A7 | 8.13 | 3.99 | 1.34 | |
| R8 | 7.67 | 3.97 | 1.74 | Nε 7.07; γ1 1.60; γ2 1.49; δ 3.05 |
| K9 | 8.05 | 3.88 | 1.75 | γ 1.33 |
| D10 | 8.69 | 4.52 | β1 2.59; β2 2.77 | |
| K11 | 7.59 | 4.14 | 1.86 | NH 7.86, ε 3.54, γ 1.51, δ 2.52 |
| R12 | 7.82 | 3.97 | 1.82 | Nε 7.16; γ1 1.57; γ2 1.67; δ 3.10 |
| K13 | 7.51 | 4.01 | 1.85 | nd |
| L14 | 7.76 | 4.03 | 1.63 | δ 0.80, γ 1.56 |
| D15 | 8.18 | 4.53 | β1 2.58, β2 2.85 | |
| NT1 | 7.21 | | | |
| NT2 | 6.99 | | | | nd refers to signals that were not observed.

TABLE 6

$^1$H NMR (600 MHz) resonance assignments derived through analysis of 2D NMR spectra and chemical shifts (δ (ppm)) for SEQ ID NO: 7 in 90% H$_2$O:10% D$_2$O at 288K.

| Residue | αNH | Hα | Hβ | Others |
|---|---|---|---|---|
| Phe (1) | | | | Ar H 7.2-7.4 |
| Gly (2) | 8.48 | 3.69 | — | — |
| Gly (3) | 7.81 | 3.67 | — | — |
| Phe(4) | 8.19 | 4.51 | 2.86, 2.93 | Ar H 7.2-7.4 |
| Thr (5) | 8.11 | 4.01 | 1.00 | |
| Gly (6) | 7.87 | 3.98 | — | — |
| Lys (7) | 7.91 | 4.00 | 1.62 | Hγ 1.09<br>Hδ 1.27 1.35<br>Hε 1.36, 1.48 |
| Arg (8) | 8.24 | 3.88 | 1.64 | Hγ 1.39, 1.50<br>Hδ 2.92<br>NHε 7.02<br>Hγ 1.13, 1.19 |

TABLE 6-continued

¹H NMR (600 MHz) resonance assignments derived through analysis of 2D NMR spectra and chemical shifts (δ (ppm)) for SEQ ID NO: 7 in 90% H₂O:10% D₂O at 288K.

| Residue | αNH | Hα | Hβ | Others |
|---|---|---|---|---|
| Lys (9) | 7.67 | 3.85 | 1.66 | Hδ 1.46 1.52 |
|  |  |  |  | Hε 2.74 |
| Ser (10) | 8.01 | 3.70 | 3.60 | — |
| Asp (11) | 8.62 | 4.54 | 2.64, 2.52 | — |
| Arg (12) | 7.63 | 4.04 | 1.66 | Hγ 1.44, 2.94 |
|  |  |  |  | NHε 7.06 |
|  |  |  |  | Hγ 1.16, 1.22 |
| Lys (13) | 7.85 | 4.03 | 1.69 | Hδ 1.48 |
|  |  |  |  | Hε 2.82 |
|  |  |  |  | Hγ 2.55, 3.18 |
| Lys (14) | 7.89 | 3.99 | 2.47 | Hδ 1.63 |
|  |  |  |  | Hε 2.58, 3.30 |
| Ala (15) | 8.03 | 3.87 | 1.25 | — |
| Asn (16) | 7.78 | 4.34 | 2.66 | — |
| Gln (17) | 7.95 | 3.92 | 2.20 | Hγ 2.13 |
| Asp (18) | 8.16 | 4.43 | 2.69, 2.44 | — |
| NH$_{T1}$ | 7.15 |  |  |  |
| NH$_{T2}$ | 6.96 |  |  |  |

TABLE 7

¹H NMR (600 MHz) resonance assignments derived through analysis of 2D NMR spectra and chemical shifts (δ (ppm)) for SEQ ID NO: 8 in 90% H₂O 10% D₂O at 288K.

| Residue | αNH | Hα | Hβ | Others |
|---|---|---|---|---|
| Phe (1) | — | 4.21 (7.2)** | 3.11, 3.14 | 2,6H 7.21 |
|  |  |  |  | 3,5H 7.31 |
|  |  |  |  | 4H 7.25 |
| Gly (2) | 8.60 (5.8)* | 3.83 | — | — |
| Gly (3) | 7.95 (5.9)* | 3.80 | — | — |
| Phe(4-F) (4) | 8.33 (6.8)* | 4.59 | 2.96, 3.02 | 2,6H 7.16 |
|  |  |  |  | 3,5H 6.98 |
| Thr (5) | 8.19 (7.1)* | 4.16 | 4.12 | Hγ 1.11 |
| Gly (6) | 8.12 (5.4)* | 3.83 | — | — |
| Lys (7) | 8.08 (5.7)* | 4.12 | 1.74 | Hγ 1.19 |
|  |  |  |  | Hδ 1.39, 1.47 |
|  |  |  |  | Hε 2.68, 3.45 |
|  |  |  |  | NHζ 8.07 |
| Arg (8) | 8.40 (4.1)* | 4.02 | 1.74 | Hγ 1.51, 1.63, |
|  |  |  |  | Hδ 3.08, |
|  |  |  |  | NHε 7.12 |
| Lys (9) | 7.76 (5.4)* | 4.07 | 1.76 | Hγ 1.28, 1.34 |
|  |  |  |  | Hδ 1.61, 1.66 |
|  |  |  |  | Hε 2.89 |
| Ser (10) | 8.23 (5.3)* | 4.12 | 3.80 | — |
| Asp (11) | 8.64 (5.3)* | 4.65 | 2.62, 2.76 | — |
| Arg (12) | 7.86 (5.6)* | 4.10 | 1.79 | Hγ 1.59, Hδ 3.09, |
|  |  |  |  | NHε 7.16 |
|  |  |  |  | Hγ 1.32, 1.41 |
| Lys (13) | 8.05 (5.3)* | 4.12 | 1.77 | Hδ 1.61 |
|  |  |  |  | Hε 2.90 |
|  |  |  |  | Hγ 1.24, 1.41 |
| Lys (14) | 8.04 (5.3)* | 4.15 | 1.82 | Hδ 1.75 |
|  |  |  |  | Hε 2.69, 3.44 |
|  |  |  |  | NHζ 8.00 |
| Lys (15) | 8.22 (6.0)* | 4.01 | 1.77 | Hγ 1.37 |
|  |  |  |  | Hδ 1.60 |

TABLE 7-continued

¹H NMR (600 MHz) resonance assignments derived through analysis of 2D NMR spectra and chemical shifts (δ (ppm)) for SEQ ID NO: 8 in 90% H₂O 10% D₂O at 288K.

| Residue | αNH | Hα | Hβ | Others |
|---|---|---|---|---|
| Asn (16) | 7.88 (6.2)* | 4.50 | 2.76 | — |
| Gln (17) | 8.21 (5.3)* | 4.05 | 2.01 | Hγ 2.32 |
| Asp (18) | 8.30 (7.2)* | 4.59 | 2.59, 2.81 | — |
| NH$_{T1}$ | 7.24 | — | — | — |
| NH$_{T2}$ | 7.21 | — | — | — |

The distance restraints used in calculating a solution structure for SEQ ID NOs:6, 7 and 8 in water were derived from NOESY spectra recorded at 298K or 288K by using mixing time of 250-350 ms. NOE cross-peak volumes were classified manually as strong (upper distance constraint≤2.7 Å), medium (≤3.5 Å), weak (≤5.0 Å) and very weak (≤6.0 Å) and standard pseudoatom distance corrections were applied for non-stereospecifically assigned protons. To address the possibility of conformational averaging, intensities were classified conservatively and only upper distance limits were included in the calculations to allow the largest possible number of conformers to fit the experimental data. Backbone dihedral angle restraints were inferred from $^3J_{NHCH\alpha}$ coupling constants in 1D spectra at 288 K, φ was restrained to −65±30° for $^3J_{NHCH\alpha}$≤6 Hz. Starting structures with randomized φ and ψ angles and extended side chains were generated using an ab initio simulated annealing protocol. The calculations were performed using the standard force field parameter set (PARALLHDG5.2.PRO) and topology file (TOPALLHDG5.2.PRO) in XPLOR with in house modifications to generated lactam bridges between lysine and aspartic acid residues and unnatural amino acid Alanine-1-naphathol. Refinement of structures was achieved using the conjugate gradient Powell algorithm with 1000 cycles of energy minimization and a refined force field based on the program CHARMm. Structures were visualized with InsightII and analyzed for distance (>0.2 Å) and dihedral angle (>2°) violations using noe.inp and noe2emin.inp files. Final structures contained no distance violations (>0.2 Å) or angle violations (>5°).

The 1D and 2D ¹H NMR of SEQ ID NOs:6, 7 and 8 showed the solution structures are very similar with highly α-helical structures in the constrained regions with 2-3 well defined helical turns.

Example 3

Circular Dichroism Spectrocopy

CD measurements were performed using a Jasco model J-710 spectropolarimeter which was routinely calibrated with (1S)-(+)-10-camphorsulfonic acid. A stock solution of 1-2 mg of peptide was dissolved in 1 mL of water. Separate 500 μL solutions of 50, 100, 200 and 400 μM were then prepared using an appropriate amount of stock solution and making up the different with 10 mM Phosphate Buffer (final pH 7.1). Spectra were recorded at room temperature (298 K), with a 0.1 cm. Jasco quartz cell over the wavelength range 260-185 nm at 100 nm/min. with a bandwidth of 1.0 nm, response time of 2 s, resolution step width of 1 nm and sensitivity of 20-50 Mdeg. Each spectrum represents the average of 5 scans. Spectra were analyzed using the spectral analysis software and smoothed using 'adaptive smoothing' function. Concentrations were determined using the PULCON method. [Wider, Dreier, 2006, *J. Am. Chem. Soc.* 128:2571-2576]

The results are shown in Table 8.

TABLE 8

CD spectral data of nociceptin peptide analogue in 10 mM phosphate buffer (pH 7.4) at 22° C.

| SEQ ID NO: | Sequence | $f_H$ (buffer) | $\theta_{222/208}$ (buffer) | $f_H$ (TFE*) |
|---|---|---|---|---|
| 1 | H-FGGFTGARKSARKLANQ-OH | 0.02 | -0.18 | 0.15 |
| 2 | H-FGGFTGARKSARKLANQ-NH$_2$ | 0.02 | -0.16 | 0.10 |
| 3 | H-FGGF(4-F)TGARKSARKLKNQ-NH$_2$ | 0.02 | -0.10 | 0.10 |
| 4 | H-FGGFTGK(Ac)RKSNRKK(Ac)ANQN-NH$_2$ | 0.03 | 0.03 | 0.13 |
| 5 | H-FGGFTGARKSARKAANQA-NH$_2$ | 0.02 | -0.11 | 0.21 |
| 6 | H-FGGFT[KARKD][KRKLD]-NH$_2$ | 0.54 | 1.00 | ND |
| 7 | H-FGGFTG[KRKSD]RK[KANQD]-NH$_2$ | 0.32 | 0.91 | ND |
| 8 | H-FGGF(4-F)TG[KRKSD]RK[KKNQD]-NH$_2$ | 0.45 | 0.90 | 0.93# |
| 9 | BzlGlyGGFTGARKSARKLKNQ-NH$_2$ | 0.04 | 0.05 | 0.24 |
| 10 | BzlGlyGGF(4-F)TGARKSARKLKNQ-NH$_2$ | 0.03 | 0.02 | 0.25 |
| 11 | BzlGlyGGFTGARKSARK-NH$_2$ | 0.03 | -0.10 | 0.10 |
| 12 | BzlGlyGGFTG[KRKSD]RK[KKNQD]-NH$_2$ | 0.41 | 0.93 | ND |
| 13 | BzlGlyGGF(4-F)TG[KRKSD]RK[KKNQD]-NH$_2$ | 0.39 | 0.94 | ND |
| 14 | BzlGlyGGFT[KARKD][KRKLD]-NH$_2$ | 0.77 | 1.00 | ND |
| 15 | Ac-[KRKSD]RK[KKNQD]-NH$_2$ | 0.60 | 0.93 | ND |
| 16 | H-TG[KRKSD]RK[KKNQD]-NH$_2$ | 0.34 | 1.12 | 0.42 |

* A mixture of buffer: TFE 50:50 was used in these experiments; ND refers to not determined; $f_H$ calculated based on θ at 222 nm (k = 2.4). [See Luo P. Baldwin R. L. (1997). Mechanism of helix induction by trifluoroethanol: a framework for extrapolating th helix-forming properties of peptides from trifluoroethanol/water mixtures back to water. Biochemistry, 36: 8413-8421]
Determined at 25° C.

All linear peptides (SEQ ID NOs:1-5, 9 and 10) showed minimal helicity in 10 μM phosphate buffer whilst addition of 2,2,2-trifluoroethanol (TFE) only marginally increased helicity. The incorporation of two lactam bridges induced appreciable helicity, monitored at 222 nm, and was calculated to range between 32-77% helicity. By comparison, the unconstrained nociceptin peptides (SEQ ID NOs:1-5, 9 and 10) had less than 6% α-helicity in water. The use of the lactam bridges did not however induce 100% helicity since in most compounds only a third to half of the peptide sequence became helical. This is due to the fact that residues 1-6 (or 1-5 in 6) are not constrained and would not be expected to be in a helical conformation as they feature amino acids that have little or no propensity to adopt helices in proteins. To determine whether the exocyclic regions were the sole cause of low helicity, SEQ ID NO:15 without the N-terminal message was investigated further. This 12-residue peptide features eight residues (K, R, Q) known to favor α-helicity in proteins, and was 60% helical in phosphate buffer by CD spectral analysis. The serine residue is conserved within the sequence of many of these peptides and is known to be a helix breaker.

Example 4

Serum Stability and Haemolysis Assay

Serum Stability

Peptide stability was assessed in normal human serum (Sigma-Aldrich, NY, USA). The peptides were incubated with the serum in a water bath at 37° C. and aliquots were removed at specific time points. Serum proteins were precipitated after adding 3-fold excess acetonitrile, and proteins were precipitated by centrifugation at 17,000 rpm for 15 min. The supernatants were collected and analyzed by LCMS (4000 QTRAPR, Applied Biosystems) and all data normalized to the initial time point.

Haemolysis Assay

Human erythrocytes were obtained from the Australian Red Cross Blood Service and diluted with PBS (pH 7.4) 1:50 to give a positive control reading of between 1.5-2.0 at 544 nm.

Equal amounts of cells were incubated with various concentrations of peptides and incubated at 37° C. for 1 hour.

Cells were pelleted by centrifugation at 17,000 rpm for 5 minutes on a bench top centrifuge and the supernatant was collected. Haemolysis was assessed by reading the absorbance at 544 nm and normalized to 0% (PBS) and 100% (0.1% Triton-X100). This work was done with UQ ethics (200600011) and ARCBS (08-01QLD-07) approval.

SEQ ID NOs:7 and 8 had significantly improved half-lives in normal human serum ($t_{1/2}$>6 h) over native nociceptin (SEQ ID NO:1, $t_{1/2}$≤1 h). Neither of the cyclic peptides tested (SEQ ID NOs:7 AND 8), nor the unconstrained nociceptin (1-17)-OH (SEQ ID NO:1) had any haemolytic activity.

Example 5

Functional Activity Assessed by ERK Phosphorylation

Neuro-2a cells were a gift from Professor John Mattick's laboratory (Institute of Molecular Bioscience, University of Queensland) and were cultured in Gibco® DMEM (Invitrogen, CA, USA) supplemented with 10% FBS (Invitrogen, CA, USA), GIBCO® Pen/Strep (50 units/mL penicillin and 50 µg/mL streptomycin, Invitrogen, CA, USA) and GIBCO® NEAA (1× concentration, Invitrogen, CA, USA). Cells were split 1:10 every 3 days.

All cells were incubated at 37° C. and 5% $CO_2$. When treated with pertussis toxin (PTX, catalogue number P7208, Sigma-Aldrich, NY, USA), cells were incubated with 500 ng/mL for 15 hours before use. Cells treated with MEK inhibitor PD98059 (catalogue number PHZ1164, Invitrogen, CA, USA) were preincubated with 50 µM for 1 hour before use.

The optimal concentration for pERK response of cells was determined to be 80,000 cells/well, plated in 2 mL of medium. This initial cell concentration allowed cells to grow but prevented 100% confluency at the end of the incubation period. Cells were placed in 12-well plates (NUNC™, NY, USA) and allowed to adhere for 24-36 h. Medium was removed and replaced with serum free media for 12-15 h prior to use. Initially, cells were challenged with compounds for increasing time periods and 35 minutes was found to be optimal to initiate pERK signaling. For agonist assays, cells were challenged with compounds for 35 minutes and incubated at 37° C. (5% $CO_2$). For antagonist assays, cells were pre-incubated with test compound for 15 minutes (incubated at 37° C., 5% $CO_2$) and then challenged with 100 nM nociceptin(1-17)-$NH_2$ (SEQ ID NO:2) for 35 minutes.

pERK Assessment Using Western Blot.

Membranes were washed 3×10 minutes with TBE (with 0.1% Tween-20) and incubated with a primary antibody. For pERK, rabbit polyclonal ERK1+2 [pTpY185/187] (1:1000, catalogue number, 44-680G, Invitrogen, CA, USA) was initially used, but later an alternative was sought due to significant batch variations. Instead, rabbit IgG Phospho-ERK1 (T202/Y204)/ERK2 (T185/Y187) (1:2000, catalogue number AF1018, R&D Systems, MN, USA) was used. For a loading control, rabbit polyclonal ERK 1/2 PAN antibody (total ERK) antibody (1:1000, catalogue number 44-654G, Invitrogen, CA, USA) was used for 1 hour. Membranes were washed as described and incubated with the secondary goat anti-rabbit IgG—HRP antibody (1:5,000; catalogue number A6667, Sigma-Aldrich, NY, USA) for 1 hour. After multiple washes, the membranes were developed using ECL Detection Solution (Amersham Biosciences) and visualized using photographic film. Radiography was quantified using ImageJ (ImageI 1.36b, NIH).

pERK Assessment Using AlphaScreen Surefire Assay (PerkinElmer, MA, USA):

pERK and total ERK concentrations were determined using a modified protocol for the AlphaScreen Surefire Assay. The modified protocol used half the volume of reagents recommended in the manufacturers' protocol with 2 µL of cell extract in both pERK and total ERK assays. The ratio of pERK to total ERK was determined using equation 1 and normalized to control. For agonist responses, the controls used were PBS (0%) and 1 µM nociceptin1-17-OH (100%). For antagonist responses, the controls used were PBS (100%) and 100 nM nociceptin1-17-$NH_2$ (100%).

$$pERK\text{:total } ERK = \frac{pERK \text{ signal}}{\text{total } ERK \text{ signal}} \qquad \text{Eq. 1}$$

Concentration responses were analyzed using non-linear regression (variable slope) (Prism5, GraphPad Software) and data is presented as either $EC_{50}$ (for agonists) or $IC_{50}$ (antagonists).

$$Y = \frac{\text{bottom} + (\text{top-bottom})}{(1 + 10^{logEC_{50}-X)\cdot hillslope})} \qquad \text{Eq. 2}$$

where $EC_{50}$ can also be $IC_{50}$, depending on the type of experiment.

The results are shown for agonists in Table 9 and antagonists in Table 10.

TABLE 9

Nociceptin analogues and their agonist pERK activity.

| SEQ ID NO: | Sequence | -log $EC_{50}$ ± SEM | $EC_{50}$ (nM) | $E_{max}$ (%) |
|---|---|---|---|---|
| 1 | H-FGGFTGARKSARKLANQ-OH | 7.94 ± 0.16 | 11 | 90 ± 7 |
| 2 | H-FGGFTGARKSARKLANQ-$NH_2$ | 7.89 ± 0.09 | 13 | 103 ± 6 |
| 3 | H-FGGF(4-F)TGARKSARKLKNQ-$NH_2$ | 9.44 ± 0.12 | 0.36 | 108 ± 9 |
| 4 | H-FGGFTGK(Ac)RKSNRKK(Ac)ANQN-$NH_2$ | 6.45 ± 0.08 | 360 | 99 ± 8 |
| 5 | H-FGGFTGARKSARKAANQA-N $H_2$ | 8.42 ± 0.15 | 4 | 93 ± 7 |
| 6 | H-FGGFT[KARKD][KRKLD]-$NH_2$ | 8.51 ± 0.14 | 3 | 96 ± 8 |

TABLE 9-continued

Nociceptin analogues and their agonist pERK activity.

| SEQ ID NO: | Sequence | -log EC$_{50}$ ± SEM | EC$_{50}$ (nM) | E$_{max}$ (%) |
|---|---|---|---|---|
| 7 | H-FGGFTG[KRKSD]RK[KANQD]-NH$_2$ | 9.22 ± 0.08 | 0.61 | 94 ± 3 |
| 8 | H-FGGF(4-F)TG[KRKSD]RK[KKNQD]-NH$_2$ | 10.40 ± 0.11 | 0.04 | 101 ± 6 |

TABLE 10

Nociceptin analogues and their antagonist pERK activity.

| SEQ ID NO: | Sequence | -log IC$_{50}$ ± SEM | IC$_{50}$ (nM) | E$_{max}$ (%) |
|---|---|---|---|---|
| 9 | BzlGlyGGFTGARKSARKLKNQ-NH$_2$ | 7.40 ± 0.11 | 39 | 103 ± 6 |
| 10 | BzlGlyGGF(4-F)TGARKSARKLKNQ-NH$_2$ | 7.49 ± 0.09 | 32 | 101 ± 4 |
| 11 | BzlGlyGGFTGARKSARK-NH$_2$ | 6.22 ± 0.08 | 755 | 87 ± 4 |
| 12 | BzlGlyGGFTG[KRKSD]RK[KKNQD]-NH$_2$ | 7.91 ± 0.10 | 12 | 98 ± 6 |
| 13 | BzlGlyGGF(4-F)TG[KRKSD]RK[KKNQD]-NH$_2$ | 8.12 ± 0.11 | 7.55 | 89 ± 5 |
| 14 | BzlGlyGGFT[KARKD][KRKLD]-NH$_2$ | <7 | IA[#] | — |
| 15 | Ac-KRKSD]RK[KKNQD]-NH$_2$ | <7 | IA[#] | — |
| 16 | H-TG[KRKSD]RK[KKNQD]-NH$_2$ | <7 | IA[#] | — |

[#]Maximum concentration tested 100 nM; IA = inactive.

Helix constrained and unconstrained peptides were pre-screened using the pERK assay at a single concentration. Compounds were tested as an agonist at 1 µM, and as antagonists at 10 µM challenged with 100 nM nociceptin(1-17)-NH$_2$. The ratio of [pERK:total ERK] was determined by western blot, quantification of densitometry proved to be quite noisy so data was interpreted in a qualitative rather than quantitative manner.

Those residues with phenylalanine at position 1 appeared to have agonist activity, whereas those, with N-tetrapeptide truncation or Phe1BzlGly substitution exhibited no agonist activity. For antagonists, a decrease in the pERK/total ERK ratio from 100 nM nociceptin was sought and those compounds that had previously shown independent agonist activity were excluded. Those residues with Phe1BzlGly substitution appeared to have antagonist activity, whereas those with native Phe1 residue were not antagonists (independent of agonist response).

Compounds were then tested further for agonist activity over a range of concentrations. Wild type nociceptin(1-17)-OH (SEQ ID NO:1) was equipotent with the amidated analogue (SEQ ID NO:2) at 11 nM, and modifications PheΔ4(pF)Phe and AlaΔ15Lys (SEQ ID NO:3) improved potency 30-fold (p≤0.001) to EC$_{50}$ 360 pM (log EC$_{50}$ −9.44±0.12).

SEQ ID NO:6 (back-to-back lactam bridge) showed improved activity over the unconstrained SEQ ID NO:2 to EC$_{50}$ 3 nM (log EC$_{50}$ −8.51±0.14, p≤0.05), whereas spacing the K(i)→D(i+4) bridges apart further improved activity to EC$_{50}$ 610 pM (SEQ ID NO:7, log EC$_{50}$ −9.22±0.08).

The cyclization strategy of SEQ ID NO:7 was identified as the most favorable strategy for agonist activity. Thus, SEQ ID NO:7 was modified to include PheΔ4(pF)Phe and AlaΔ15Lys substitutions (SEQ ID NO:8) shown to improve activity (SEQ ID NOs:3 vs 2). These substitutions significantly increased agonist activity to afford agonist SEQ ID NO:8 (EC$_{50}$ 40 pM) significantly improved relative to SEQ ID NO:7 (EC$_{50}$ 610 pM) and its unconstrained analogue SEQ ID NO:3 (EC$_{50}$ 360 pM; p≤0.001). To establish that the increased agonist activity for SEQ ID NOs:7 and 8 was not due to replacement of amino acids, SEQ ID NOs:4 and 5 were designed where those amino acids involved in K(i)→D(i+4) lactam bridges (amino acids 7, 11, 14 and 18) were replaced with either alanines (SEQ ID NO:5) or Lys/Asn (SEQ ID NO:4). The positively charged amine of lysine side chain was capped with an acetyl group to remove the charge to more effectively mimic the lactam bridging residues. Asparagine rather than aspartic acid was used to maintain the length of the side chain, while removing the negative charge of the carboxylic acid moiety. By replacing these residues with alanines in SEQ ID NO:5; agonist activity was altered (EC$_{50}$ 4 nM) relative to SEQ ID NO:2 but this difference was not deemed significant (p≥0.05). However, replacement with Lys(Ac)/Asn significantly decreased the potency of the compound (EC$_{50}$ 360 nM, p≤0.001). This suggests that replacement of these charged residues to form the lactam bridge did not adversely affect the activity of the compound but that the Lys and Asn (isosteric to Asp) residues may actually have hindered the activity due to the large side chains or due to their destabilizing influence on the α-helix.

SEQ ID NOs:13 and 10 were also assessed for agonist activity because there is previous evidence that these compounds may have residual agonist activity despite the BzlGly moiety at position 1. [Guerrini et al., 2005, J. Med. Chem., 48:1421-1427] Constrained SEQ ID NO:13 and the linear analogue SEQ ID NO:10 were tested at a single point concentration (1 µM) and neither showed significant agonist activity.

The specificity of the most potent agonist, SEQ ID NO:8, was also investigated. Cells were pretreated with 1.5 µM SEQ ID NO:11, previously shown to be a specific ORL-1 antagonist, and then challenged with an increasing concentration of SEQ ID NO:8. The potency of SEQ ID NO:8 was significantly reduced from $EC_{50}$ 40 pM to 1 nM (p≤0.001). This suggests that the pERK agonist activity of SEQ ID NO:8 is indeed mediated through the ORL-1 receptor.

As for antagonist analogues (Table 10) four key conclusions can be made from the biological assays. SEQ ID NO:11 is significantly less potent than SEQ ID NO:9 (log $IC_{50}$ −6.24±0.15, 755 nM and log $IC_{50}$ −7.40±0.11, 39 nM respectively). SEQ ID NO:9 has an additional four residues at the C-terminal ([BzlGly1]GGFTGARKSARKLKNQ-$NH_2$) that, according to these results are significant contributors to antagonist activity. Secondly, the para-fluoro-phenylalanine substitution has been shown to improve agonist activity of nociceptin analogues, but does not enhance the antagonist activity of SEQ ID NO:9 over SEQ ID NO:10 (log $IC_{50}$ −7.40±0.11, 40 nM and log $IC_{50}$ −7.49±0.09, 32 nM respectively). It also appears that the cyclization strategies employed have a larger influence on antagonist activity. More specifically, consecutive K(6)→D(10), K(11)→D(15) lactam bridges (as in SEQ ID NO:14) abolished antagonist activity (up to 3 μM) whereas the alternative arrangement of K(7)→D(11), K(14)→D(18) in SEQ ID NO:12 enhances antagonist activity relative to the unconstrained SEQ ID NO:9 ($IC_{50}$ 12 nM and 39 nM respectively). Whilst differences in activity were expected between the cyclization strategies, complete loss of antagonist activity of SEQ ID NO:14 was not expected based on the agonist dataset (Table 8). The difference in potency in these two cyclization arrangements may be explained by the fundamental differences between them. The lack of an extra four C-terminal residues (underlined) in (BzlGGGFTG[KRKSD]RK[KKNQD] versus BzlGGGFT[KARKD][KRKLD]-$NH_2$) may fail to provide an additional binding moiety to improve affinity. Also, it must be taken into account that the changes of key residues (bold, position 6, 10, 11 and 15) to enable side chain to side chain lactam bridge formation might lead to a decrease in potency. It is also possible that the back-to-back arrangement may lead to an unfavorable interaction between the address domain and benzylglycine due to the hinge region (Thr5Gly6Ala7), an anchoring point, being compromised, which in turn results in the failure to meet the steric requirement for receptor interaction. Finally, it is possible that the side chain bridging clashes with receptor residues in the antagonist binding mode. Nevertheless, by comparing unconstrained SEQ ID NO:9 and constrained SEQ ID NO:12, the improvement in antagonist activity is three-fold. Similarly, constrained SEQ ID NO:13 is over four-fold more potent than the unconstrained SEQ ID NO:10. Based on the alanine mutants in the agonist dataset (discussed above), we are confident that this enhancement in activity is due to the induction of helical structure in SEQ ID NOs:12 and 13, rather than substitution of residues at positions 7, 11, 14 and 18. In addition, it is important to note the difference in enhanced of biological activities between agonist and antagonist analogues after α-helicity induction. In the agonist series, an improvement of 20-fold has been obtained, while for the antagonist series the improvement is 5-fold. A possible explanation may be rationalized by the presence of the N-BzlGly substitution at position 1. Data recently published by Guerrini et al have suggested that [BzlGly1]nociceptin(1-17)-$NH_2$ may bind to ORL-1 in a slightly different orientation or conformation relative to nociceptin(1-17)-$NH_2$. [Guerrini et al., 2005, *J. Med. Chem.*, 48:1421-1427; Guerrini et al., 2000, *J. Med. Chem.*, 43:2805-2813]. This assertion could explain why different enhancements in activity were observed between the agonists and antagonists in the dataset with the agonist and antagonist binding at different or overlapping sites in the receptor.

Example 6

Anti-Nociceptive Activity of ORL-1 Agonists and Antagonists in Mice

As a demonstration of in vivo activity for helix-constrained peptides, the most potent agonist (SEQ ID NO:8) was administered at 200 pmol per front paw to mice (n=6-8/treatment group). A similar dose has been used before by others for nociceptin (NC, SEQ ID NO:1) itself in similar assays with some activity ($EC_{50}$=200 pmol). Herein nociceptin as the amide (SEQ ID NO:2) and the more potent peptide agonist analogue (SEQ ID NO:3) were used for comparison against SEQ ID NO:8 and similarly administered at 200 pmol per paw to separate groups of mice.

Protocol:

Mice (C57BL/6; n=45) were brought into the experimental room for at least 30 minutes prior to testing. They were then individually placed on an accredited hot plate heated to 53±0.54° C. and timed until any front paw withdrawal, licking or jumping behaviour was recorded (baseline response). Mice were not left on the hot plate for longer than 30 sec. Mice were then injected intraplantar into both front paws with either 200 pmol of SEQ ID NO:2 or SEQ ID NO:3 NC or SEQ ID NO:8 or saline vehicle. Mice were then individually placed on the hot plate again at time points 1, 5, 15, 30, 45 and 60 min post injection. Each test was video monitored.

In a parallel experiment, agonist of SEQ ID NO:8 was co-administered with the helical antagonist of SEQ ID NO:13, where upon the increased paw withdrawal latency produced by agonist of SEQ ID NO:8 alone was abolished. This confirms that the helix constrained peptide of SEQ ID NO:13 is a potent antagonist of SEQ ID NO:8 in vivo.

Figure 2:
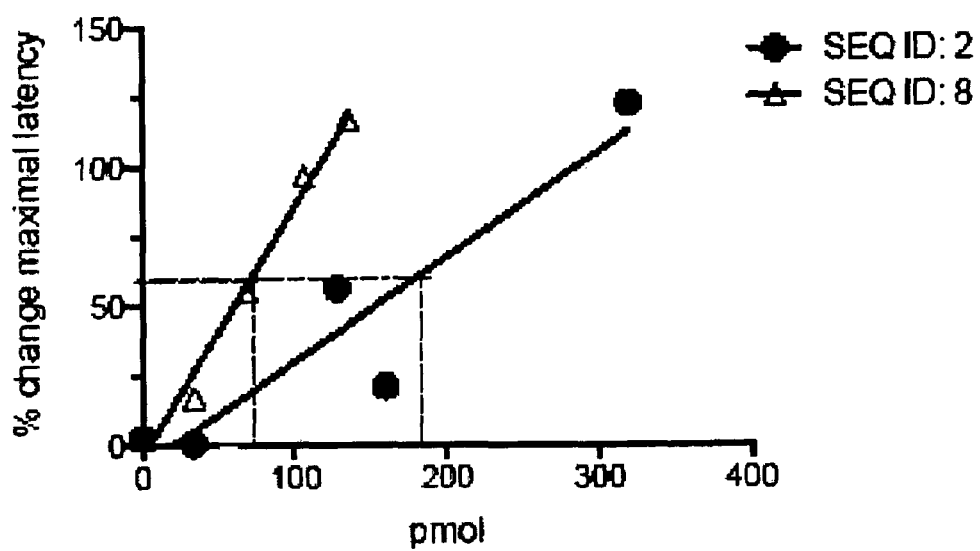
FIG. 2 is a graphical representation showing dose response curves of SEQ ID NO:8 ($ED_{50}$=70 pmol) and SEQ ID NO:2 ($ED_{50}$=184 pmol) demonstrating that SEQ ID NO:8 is a more potent agonist.

Results:

The results are shown in FIG. 1 and FIG. 2.

SEQ ID NO:2 at 200 pmol successfully prevented the hot plate sensitization at 1 min slightly but significantly raising the thermal nociceptive threshold by ~20%, although this effect was absent by 5 minutes. On the other hand, SEQ ID NO:3 at 200 pmol showed a slightly longer duration of anti-nociceptive activity at 5 minutes, but this effect was missing by 15 minutes.

By contrast with the above peptides, the helix-constrained compound (SEQ ID NO:8), administered at the same dose as SEQ ID NO:2 and SEQ ID NO:3, clearly resulted in a much more significant and prolonged thermal anti-nociception, where animals showed an increase of ~100% in paw withdrawal latency after 5 minutes. The anti-nociceptive effect caused by SEQ ID NO:8 was longer lived (greater than 45 min) than that observed by SEQ ID NO:2 and SEQ ID NO:3 and even nociceptin itself (SEQ ID NO:1), which appeared to have no effects after 5 min.

Interpretation:

The experimental helix constrained peptide (SEQ ID NO:8) was significantly more potent than the unconstrained linear endogenous peptides as anti-nociceptive agents in vivo, enabling treated mice to maintain forepaw contact with a hotplate for longer periods of time than sham mice or nociceptin-treated mice. The helix-constrained peptide is sufficiently stable in vivo in this model of thermal hyperalgesia to demonstrate clear superior properties to the linear endogenous peptides when agonist of SEQ ID NO:8 was co-administered (at $ED_{100}$=200 pmol) with helical antagonist of SEQ ID NO:13 (200 pmol), the increased paw withdrawal latency produced by SEQ ID NO:8 alone was abolished, confirming that helix constrained peptide SEQ ID NO:13 is a potent antagonist of agonist SEQ ID NO:8 in vivo (FIG. 1).

FIG. 2 compares the concentration response plots for the anti-nociceptive effects of helix constrained agonist SEQ ID NO:8 ($ED_{50}$=70 pmol) vs linear peptide SEQ ID NO:2 ($ED_{50}$=184 pmol). This demonstrates a significant increase in agonist potency for the helix constrained agonist SEQ ID NO:8.

The invention claimed is:

1. A peptide of formula (I):

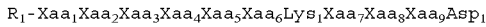

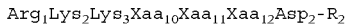

(I)

wherein
Xaa₁ is Phe or N-BzlGly;
Xaa₂ is Gly;
Xaa₃ is Gly or Ala;
Xaa₄ is Phe or 4-R₃-Phe;
Xaa₅ is Thr or Ser;
Xaa₆ is selected from Gly, L-Ala, L-Ser, L-Lys, L-Arg, L-Pro, L-Glu, L-Ile, L-Met and L-Val;
Xaa₇ is selected from L-Arg, L-Lys, L-Orn, L-Ala, L-Leu, L-Met, L-Glu, L-Gln, L-Cys, L-Val, L-Ile, L-Phe, L-Tyr, L-Trp, L-Thr, L-Ser and L-Asp;
Xaa₈ is selected from L-Lys, L-Orn, L-Arg, L-His, L-2,3-diaminopropionic acid and L-2,4-diaminobutanoic acid;
Xaa₉ is selected from L-Ser, L-Thr, L-Cys, L-Asn, L-Gln, L-Tyr, L-Ala, L-Val, L-Leu, L-Ile, L-Met, L-Phe, L-Trp and L-Arg;
Xaa₁₀ is selected from L-Ala, L-Lys, L-Arg, L-Orn, L-Leu, L-Ile, L-Val, L-Met, L-Phe, L-Trp, L-Ser, L-Thr, L-Cys, L-Gln, L-Asn, L-Tyr and L-His;
Xaa₁₁ is selected from L-Asn, L-Ser, L-Thr, L-Cys, L-Gln, L-Tyr, L-Ala, L-Val, L-Leu, L-Ile, L-Met, L-Phe and L-Trp;
Xaa₁₂ is selected from L-Gln, L-Asn, L-Arg, L-Lys, L-Ser, L-Thr, L-Cys, L-Tyr, L-Ala, L-Val, L-Leu, L-Ile, L-Met, L-Phe and L-Trp;
R₁ is hydrogen or an N-terminal capping group, with the proviso that when Xaa₁ is N-BzlGly, R₁ is absent;
R₂ is —OH or a C-terminal capping group; and
R₃ is an electron withdrawing substituent;
wherein the side chains of Lys₁ and Asp₁ are linked to form a lactam bridge and the side chains of Lys₃ and Asp₂ are linked to form a lactam bridge;
or a pharmaceutically acceptable salt thereof.

2. The peptide according to claim 1 wherein R₂ is —NH₂ or —NH(C₁₋₆alkyl).

3. The peptide according to claim 1 wherein Xaa₅ is L-Thr.

4. The peptide according to claim 1 wherein Xaa₆ is selected from Gly, L-Lys, L-Ala, L Arg and L-Glu.

5. The peptide according to claim 4 wherein Xaa₆ is Gly or L-Lys.

6. The peptide according to claim 4 wherein Xaa₇ is L-Arg or L-Lys.

7. The peptide according to claim 1 wherein Xaa₈ is L-Lys.

8. The peptide according to claim 1 wherein Xaa₉ is L-Ser.

9. The peptide according to claim 1 wherein Xaa₁₀ is selected from L-Ala, L-Leu, L-Lys, L-Arg and L-Asn.

10. The peptide according to claim 1 wherein Xaa₁₁ is selected from L-Asn, L-Gln and L-Ala.

11. The peptide according to claim 1 wherein Xaa₁₂ is selected from L-Gln, L-Asn, L-Arg and L-Lys.

12. The peptide according to claim 1 wherein R₃ is selected from —F, —Cl, —Br, —I, —CN, —CF₃, —NH₂, —N(CH₃)₂, —NO₂, —CHO and —COalkyl.

13. The peptide according to claim 12 wherein R₃ is selected from —F and —NO₂.

14. The peptide according to claim 1 which is a peptide of formula (II):

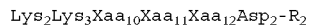

(II)

wherein
Xaa₁ is Phe or N-BzlGly;
Xaa₄ is Phe or 4-R₃Phe;
and R₁, R₂, R₃, Xaa₆, Xaa₇, Xaa₈, Xaa₉, Xaa₁₀, Xaa₁₁ and Xaa₁₂ are as defined for formula (I).

15. The peptide according to claim 1 wherein Xaa₁ is L-Phe, Xaa₂ is Gly, Xaa₃ is Gly and Xaa₄ is L-Phe or L-4-R₃-Phe.

16. The peptide according to claim 1 which is a peptide of formula (III):

R₁-PheGlyGlyXaa₄ThrXaa₆Lys₁Xaa₇Xaa₈Xaa₉Asp₁Arg₁

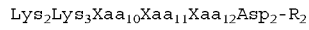

(III)

wherein R₁, Xaa₄, Xaa₆, Xaa₇, Xaa₈, Xaa₉, Xaa₁₀, Xaa₁₁, Xaa₁₂ and R₂ are as defined in formula (I).

17. The peptide according to claim 1 which is a peptide of formula (IV):

R₁-Xaa₁Xaa₂Xaa₃Xaa₄Xaa₅Xaa₆Lys₁Xaa₇Xaa₈Xaa₉Asp₁

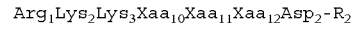

(IV)

wherein
Xaa₁ is N-BzlGly;
and Xaa₂, Xaa₃, Xaa₄, Xaa₅, Xaa₆, Xaa₇, Xaa₈, Xaa₉, Xaa₁₀, Xaa₁₁, Xaa₁₂ R₁ and R₂ are as defined for formula (I).

18. The peptide according to claim 1 selected from:

```
                                      SEQ ID NO: 7
H-FGGFTG[KRKSD]RK[KANQD]-NH₂

SEQ ID NO: 8
H-FGGFTG[KRKSD]RK[KKNQD]-NH₂

SEQ ID NO: 17
H-FGGFTG[KRKSD]RK[KANQD]-OH

SEQ ID NO: 18
H-FGGFTG[KRKSD]RK[KKNQD]-OH

SEQ ID NO: 12
BzlGlyGGFTG[KRKSD]RK[KKNQD]-NH₂

SEQ ID NO: 13
BzlGlyGGF(4F)TG[KRKSD]RK[KKNQD]-NH₂

SEQ ID NO: 19
BzlGlyGGFTG[KRKSD]RK[KKNQD]-OH

SEQ ID NO: 20
BzlGlyGGF(4F)TG[KRKSD]RK[KKNQD]-OH
``` where the square brackets indicate the formation of a lactam bridge between the lysine (K) side chain amino group and the aspartic acid (D) side chain carboxy group thereby forming a macrocycle.

19. The peptide according to claim 18 selected from:

```
                               SEQ ID NO: 7
H-FGGFTG[KRKSD]RK[KANQD]-NH2

SEQ ID NO: 8
H-FGGFTG[KRKSD]RK[KKNQD]-NH2

SEQ ID NO: 12
BzlGlyGGFTG[KRKSD]RK[KKNQD]-NH2

SEQ ID NO: 13
BzlGlyGGF(4F)TG[KRKSD]RK[KKNQD]-NH2.
```

20. A pharmaceutical composition comprising a peptide according to claim 1 or a pharmaceutically acceptable salt thereof and a pharmaceutically acceptable carrier or excipient.

21. The pharmaceutical composition according to claim 20 further comprising one or more other pharmacologically active compounds selected from an opioid analgesic, a non-steroidal anti-inflammatory drug, a sedative, an NMDA receptor antagonist, an alpha-adrenergic, a tricyclic anti-depressant, a muscarinic antagonist, a COX-2 selective inhibitor, a coal-tar analgesic, a neuroleptic, a vanilloid receptor agonist, a local anaesthetic, a corticosteroid, a 5-HT receptor antagonist, Tramadol, a PDEV inhibitor, an alpha-2-delta ligand, a cannbinoid, a metabolic glutamate subtype 1 receptor antagonist, a serotonin reuptake inhibitor, a noradrenaline reuptake inhibitor, a dual serotonin-noradrenaline reuptake inhibitor, an inducible nitric oxide synthase inhibitor, an acetylcholinesterase inhibitor, a prostaglandin $E_2$ subtype 4 antagonist, a leukotriene B4 antagonist, a sodium channel blocker, a 5-HT3 antagonist, a stimulant, a non-stimulant and an amphetamine.

22. A method of producing analgesia comprising administering to a subject in need thereof, an effective amount of a peptide of claim 1 or a pharmaceutically acceptable salt thereof.

* * * * *

UNITED STATES PATENT AND TRADEMARK OFFICE
CERTIFICATE OF CORRECTION

PATENT NO. : 8,921,306 B2  
APPLICATION NO. : 13/702479  
DATED : December 30, 2014  
INVENTOR(S) : Fairlie et al.

Page 1 of 1

It is certified that error appears in the above-identified patent and that said Letters Patent is hereby corrected as shown below:

In the claims

Column 49, lines 51 to 52, Claim 6 should read:

6. The peptide according to claim 1 wherein $Xaa_7$ is L-Arg or L-Lys.

Column 50, lines 47 to 48, Claim 18 should read:

SEQ ID NO:8 H-FGGF(4F)TG[KRKSD]RK[KKNQD]-$NH_2$

Column 51, lines 6 to 7, Claim 19 should read:

SEQ ID NO:8 H-FGGF(4F)TG[KRKSD]RK[KKNQD]-$NH_2$

Signed and Sealed this  
Twenty-first Day of April, 2015

Michelle K. Lee  
*Director of the United States Patent and Trademark Office*

SEQUENCE LISTING

```
<160> NUMBER OF SEQ ID NOS: 20

<210> SEQ ID NO 1
<211> LENGTH: 17
<212> TYPE: PRT
<213> ORGANISM: Human

<400> SEQUENCE: 1

Phe Gly Gly Phe Thr Gly Ala Arg Lys Ser Ala Arg Lys Leu Ala Asn
1               5                   10                  15

Gln

<210> SEQ ID NO 2
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (17)..(17)
<223> OTHER INFORMATION: C-terminal amidated asparagine

<400> SEQUENCE: 2

Phe Gly Gly Phe Thr Gly Ala Arg Lys Ser Ala Arg Lys Leu Ala Asn
1               5                   10                  15

Xaa

<210> SEQ ID NO 3
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: 4-Fluorophenylalanine
<220> FEATURE:
<221> NAME/KEY: MISC_FEATURE
<222> LOCATION: (17)..(17)
<223> OTHER INFORMATION: C-terminal amidated glutamine

<400> SEQUENCE: 3

Phe Gly Gly Xaa Thr Gly Ala Arg Lys Ser Ala Arg Lys Leu Lys Asn
1               5                   10                  15

Xaa

<210> SEQ ID NO 4
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: 6N-acetyl lysine
<220> FEATURE:
<221> NAME/KEY: MISC_FEATURE
```

```
<222> LOCATION: (14)..(14)
<223> OTHER INFORMATION: 6N-acetyl lysine
<220> FEATURE:
<221> NAME/KEY: MISC_FEATURE
<222> LOCATION: (18)..(18)
<223> OTHER INFORMATION: C-terminal amidated asparagine

<400> SEQUENCE: 4

Phe Gly Gly Phe Thr Gly Xaa Arg Lys Ser Asn Arg Lys Xaa Ala Asn
1               5                   10                  15

Gln Xaa

<210> SEQ ID NO 5
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: C-terminal amidated alanine

<400> SEQUENCE: 5

Phe Gly Gly Phe Thr Gly Ala Arg Lys Ser Ala Arg Lys Ala Ala Asn
1               5                   10                  15

Gln Xaa

<210> SEQ ID NO 6
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: lysine with side chain amino group linked to
      position 10 by amide bond
<220> FEATURE:
<221> NAME/KEY: MISC_FEATURE
<222> LOCATION: (10)..(10)
<223> OTHER INFORMATION: aspartic acid with side chain carboxylic acid
      group linked to position 6 by amide bond
<220> FEATURE:
<221> NAME/KEY: MISC_FEATURE
<222> LOCATION: (11)..(11)
<223> OTHER INFORMATION: lysine with side chain amino group linked to
      position 15 by amide bond
<220> FEATURE:
<221> NAME/KEY: MISC_FEATURE
<222> LOCATION: (15)..(15)
<223> OTHER INFORMATION: C-terminal amidated aspartic acid with side
      chain carboxylic acid group linked to position 11 by amide bond

<400> SEQUENCE: 6

Phe Gly Gly Phe Thr Xaa Ala Arg Lys Xaa Xaa Arg Lys Leu Xaa
1               5                   10                  15

<210> SEQ ID NO 7
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: lysine with side chain amino group linked to
      position 11 by amide bond
<220> FEATURE:
```

```
<221> NAME/KEY: MISC_FEATURE
<222> LOCATION: (11)..(11)
<223> OTHER INFORMATION: aspartic acid with side chain carboxylic acid
      group linked to position 7 by amide bond
<220> FEATURE:
<221> NAME/KEY: MISC_FEATURE
<222> LOCATION: (14)..(14)
<223> OTHER INFORMATION: lysine with side chain amino group linked to
      position 18 by amide bond
<220> FEATURE:
<221> NAME/KEY: MISC_FEATURE
<222> LOCATION: (18)..(18)
<223> OTHER INFORMATION: C-terminal amidated aspartic acid with side
      chain carboxylic acid group linked to position 14 by amide bond

<400> SEQUENCE: 7

Phe Gly Gly Phe Thr Gly Xaa Arg Lys Ser Xaa Arg Lys Xaa Ala Asn
1               5                   10                  15

Gln Xaa

<210> SEQ ID NO 8
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: 4-fluorophenylalanine
<220> FEATURE:
<221> NAME/KEY: MISC_FEATURE
<222> LOCATION: (7)..(7)
<223> OTHER INFORMATION: lysine with side chain amino group linked to
      position 11 by amide bond
<220> FEATURE:
<221> NAME/KEY: MISC_FEATURE
<222> LOCATION: (11)..(11)
<223> OTHER INFORMATION: aspartic acid with side chain carboxylic acid
      group linked to position 7 by amide bond
<220> FEATURE:
<221> NAME/KEY: MISC_FEATURE
<222> LOCATION: (14)..(14)
<223> OTHER INFORMATION: lysine with side chain amino group linked to
      position 18 by amide bond
<220> FEATURE:
<221> NAME/KEY: MISC_FEATURE
<222> LOCATION: (18)..(18)
<223> OTHER INFORMATION: C-terminal amidated aspartic acid with side
      chain carboxylic acid group linked to position 14 by amide bond

<400> SEQUENCE: 8

Phe Gly Gly Xaa Thr Gly Xaa Arg Lys Ser Xaa Arg Lys Xaa Lys Asn
1               5                   10                  15

Gln Xaa

<210> SEQ ID NO 9
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-benzylglycine
<220> FEATURE:
<221> NAME/KEY: MISC_FEATURE
<222> LOCATION: (17)..(17)
<223> OTHER INFORMATION: C-terminal amidated glutamine

<400> SEQUENCE: 9
```

```
Xaa Gly Gly Phe Thr Gly Ala Arg Lys Ser Ala Arg Lys Leu Lys Asn
1               5                   10                  15

Xaa
```

<210> SEQ ID NO 10
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-benzylglycine
<220> FEATURE:
<221> NAME/KEY: MISC_FEATURE
<222> LOCATION: (4)..(4)
<223> OTHER INFORMATION: 4-fluorophenylalanine
<220> FEATURE:
<221> NAME/KEY: MISC_FEATURE
<222> LOCATION: (17)..(17)
<223> OTHER INFORMATION: C-terminal amidated glutamine

<400> SEQUENCE: 10

```
Xaa Gly Gly Xaa Thr Gly Ala Arg Lys Ser Ala Arg Lys Leu Lys Asn
1               5                   10                  15

Xaa
```

<210> SEQ ID NO 11
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = N-benzylglycine
<220> FEATURE:
<221> NAME/KEY: MISC_FEATURE
<222> LOCATION: (13)..(13)
<223> OTHER INFORMATION: C-terminal amidated lysine

<400> SEQUENCE: 11

```
Xaa Gly Gly Phe Thr Gly Ala Arg Lys Ser Ala Arg Xaa
1               5                   10
```

<210> SEQ ID NO 12
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-benzylglycine
<220> FEATURE:
<221> NAME/KEY: MISC_FEATURE
<222> LOCATION: (7)..(7)
<223> OTHER INFORMATION: lysine with side chain amino group linked to
      position 11 by amide bond
<220> FEATURE:
<221> NAME/KEY: MISC_FEATURE
<222> LOCATION: (11)..(11)
<223> OTHER INFORMATION: aspartic acid with side chain carboxylic acid
      group linked to position 7 by amide bond
<220> FEATURE:
<221> NAME/KEY: MISC_FEATURE
<222> LOCATION: (14)..(14)
<223> OTHER INFORMATION: lysine with side chain amino group linked to
      position 18 by amide bond

```
<220> FEATURE:
<221> NAME/KEY: MISC_FEATURE
<222> LOCATION: (18)..(18)
<223> OTHER INFORMATION: C-terminal amidated aspartic acid with side
      chain carboxylic acid group linked to position 14 by amide bond

<400> SEQUENCE: 12

Xaa Gly Gly Phe Thr Gly Xaa Arg Lys Ser Xaa Arg Lys Xaa Lys Asn
1               5                   10                  15

Gln Xaa

<210> SEQ ID NO 13
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-benzylglycine
<220> FEATURE:
<221> NAME/KEY: MISC_FEATURE
<222> LOCATION: (4)..(4)
<223> OTHER INFORMATION: 4-fluorophenylalanine
<220> FEATURE:
<221> NAME/KEY: MISC_FEATURE
<222> LOCATION: (7)..(7)
<223> OTHER INFORMATION: lysine with side chain amino group linked to
      position 11 by amide bond
<220> FEATURE:
<221> NAME/KEY: MISC_FEATURE
<222> LOCATION: (11)..(11)
<223> OTHER INFORMATION: aspartic acid with side chain carboxylic acid
      group linked to position 7 by amide bond
<220> FEATURE:
<221> NAME/KEY: MISC_FEATURE
<222> LOCATION: (14)..(14)
<223> OTHER INFORMATION: lysine with side chain amino group linked to
      position 18 by amide bond
<220> FEATURE:
<221> NAME/KEY: MISC_FEATURE
<222> LOCATION: (18)..(18)
<223> OTHER INFORMATION: C-terminal amidated aspartic acid with side
      chain carboxylic acid group linked to position 14 by amide bond

<400> SEQUENCE: 13

Xaa Gly Gly Xaa Thr Gly Xaa Arg Lys Ser Xaa Arg Lys Xaa Lys Asn
1               5                   10                  15

Gln Xaa

<210> SEQ ID NO 14
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-benzylglycine
<220> FEATURE:
<221> NAME/KEY: MISC_FEATURE
<222> LOCATION: (6)..(6)
<223> OTHER INFORMATION: lysine with side chain amino group linked to
      position 10 by amide bond
<220> FEATURE:
<221> NAME/KEY: MISC_FEATURE
<222> LOCATION: (10)..(10)
<223> OTHER INFORMATION: aspartic acid with side chain carboxylic acid
      group linked to position 6 by amide bond
<220> FEATURE:
<221> NAME/KEY: MISC_FEATURE
```

```
<222> LOCATION: (11)..(11)
<223> OTHER INFORMATION: lysine with side chain amino group linked to
      position 15 by amide bond
<220> FEATURE:
<221> NAME/KEY: MISC_FEATURE
<222> LOCATION: (15)..(15)
<223> OTHER INFORMATION: C-terminal amidated aspartic acid with side
      chain carboxylic acid group linked to position 11 by amide bond

<400> SEQUENCE: 14

Xaa Gly Gly Phe Thr Xaa Ala Arg Lys Xaa Xaa Arg Lys Leu Xaa
1               5                   10                  15

<210> SEQ ID NO 15
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-terminal acetylated lysine with side chain
      amino group linked to position 5 by amide bond
<220> FEATURE:
<221> NAME/KEY: MISC_FEATURE
<222> LOCATION: (5)..(5)
<223> OTHER INFORMATION: aspartic acid with side chain carboxylic acid
      group linked to position 1 by amide bond
<220> FEATURE:
<221> NAME/KEY: MISC_FEATURE
<222> LOCATION: (8)..(8)
<223> OTHER INFORMATION: lysine with side chain amino group linked to
      position 12 by amide bond
<220> FEATURE:
<221> NAME/KEY: MISC_FEATURE
<222> LOCATION: (12)..(12)
<223> OTHER INFORMATION: C-terminal amidated aspartic acid with side
      chain carboxylic acid group linked to position 8 by amide bond

<400> SEQUENCE: 15

Xaa Arg Lys Ser Xaa Arg Lys Xaa Lys Asn Gln Xaa
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: lysine with side chain amino group linked to
      position 7 by amide bond
<220> FEATURE:
<221> NAME/KEY: MISC_FEATURE
<222> LOCATION: (7)..(7)
<223> OTHER INFORMATION: aspartic acid with side chain carboxylic acid
      group linked to position 3 by amide bond
<220> FEATURE:
<221> NAME/KEY: MISC_FEATURE
<222> LOCATION: (10)..(10)
<223> OTHER INFORMATION: lysine with side chain amino group linked to
      position 14 by amide bond
<220> FEATURE:
<221> NAME/KEY: MISC_FEATURE
<222> LOCATION: (14)..(14)
<223> OTHER INFORMATION: C-terminal amidated aspartic acid with side
      chain carboxykic acid group linked to position 10 by amide bond

<400> SEQUENCE: 16

Thr Gly Xaa Arg Lys Ser Xaa Arg Lys Xaa Lys Asn Gln Xaa
1               5                   10
```

```
<210> SEQ ID NO 17
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: lysine with side chain amino group linked to
      position 11 by amide bond
<220> FEATURE:
<221> NAME/KEY: MISC_FEATURE
<222> LOCATION: (11)..(11)
<223> OTHER INFORMATION: aspartic acid with side chain carboxylic acid
      group linked to position 7 by amide bond
<220> FEATURE:
<221> NAME/KEY: MISC_FEATURE
<222> LOCATION: (14)..(14)
<223> OTHER INFORMATION: lysine with side chain amino group linked to
      position 18 by amide bond
<220> FEATURE:
<221> NAME/KEY: MISC_FEATURE
<222> LOCATION: (18)..(18)
<223> OTHER INFORMATION: aspartic acid with side chain carboxylic acid
      group linked to position 14 by amide bond

<400> SEQUENCE: 17

Phe Gly Gly Phe Thr Gly Xaa Arg Lys Ser Xaa Arg Lys Xaa Ala Asn
1               5                   10                  15

Gln Xaa

<210> SEQ ID NO 18
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: lysine with side chain amino group linked to
      position 11 by amide bond
<220> FEATURE:
<221> NAME/KEY: MISC_FEATURE
<222> LOCATION: (11)..(11)
<223> OTHER INFORMATION: aspartic acid with side chain carboxylic acid
      group linked to position 7 by amide bond
<220> FEATURE:
<221> NAME/KEY: MISC_FEATURE
<222> LOCATION: (14)..(14)
<223> OTHER INFORMATION: lysine with side chain amino group linked to
      position 18 by amide bond
<220> FEATURE:
<221> NAME/KEY: MISC_FEATURE
<222> LOCATION: (18)..(18)
<223> OTHER INFORMATION: aspartic acid with side chain carboxylic acid
      group linked to position 14 by amide bond

<400> SEQUENCE: 18

Phe Gly Gly Phe Thr Gly Xaa Arg Lys Ser Xaa Arg Lys Xaa Lys Asn
1               5                   10                  15

Gln Xaa

<210> SEQ ID NO 19
<211> LENGTH: 18
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (1)..(1)
<223> OTHER INFORMATION: N-benzylglycine
<220> FEATURE:
<221> NAME/KEY: MISC_FEATURE
<222> LOCATION: (7)..(7)
<223> OTHER INFORMATION: lysine with side chain amino group linked to
      position 11 by amide bond
<220> FEATURE:
<221> NAME/KEY: MISC_FEATURE
<222> LOCATION: (11)..(11)
<223> OTHER INFORMATION: aspartic acid with side chain carboxylic acid
      group linked to position 7 by amide bond
<220> FEATURE:
<221> NAME/KEY: MISC_FEATURE
<222> LOCATION: (14)..(14)
<223> OTHER INFORMATION: lysine with side chain amino group linked to
      position 18 by amide bond
<220> FEATURE:
<221> NAME/KEY: MISC_FEATURE
<222> LOCATION: (18)..(18)
<223> OTHER INFORMATION: aspartic acid with side chain carboxylic acid
      group linked to position 14 by amide bond

<400> SEQUENCE: 19

Xaa Gly Gly Phe Thr Gly Xaa Arg Lys Ser Xaa Arg Lys Xaa Lys Asn
1               5                   10                  15

Gln Xaa

<210> SEQ ID NO 20
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-benzylglycine
<220> FEATURE:
<221> NAME/KEY: MISC_FEATURE
<222> LOCATION: (4)..(4)
<223> OTHER INFORMATION: 4-fluorophenylalanine
<220> FEATURE:
<221> NAME/KEY: MISC_FEATURE
<222> LOCATION: (7)..(7)
<223> OTHER INFORMATION: lysine with side chain amino group linked to
      position 11 by amide bond
<220> FEATURE:
<221> NAME/KEY: MISC_FEATURE
<222> LOCATION: (11)..(11)
<223> OTHER INFORMATION: aspartic acid with side chain carboxylic acid
      group linked to position 7 by amide bond
<220> FEATURE:
<221> NAME/KEY: MISC_FEATURE
<222> LOCATION: (14)..(14)
<223> OTHER INFORMATION: lysine with side chain amino group linked to
      position 18 by amide bond
<220> FEATURE:
<221> NAME/KEY: MISC_FEATURE
<222> LOCATION: (18)..(18)
<223> OTHER INFORMATION: aspartic acid with side chain carboxylic acid
      group linked to position 14 by amide bond

<400> SEQUENCE: 20

Xaa Gly Gly Xaa Thr Gly Xaa Arg Lys Ser Xaa Arg Lys Xaa Lys Asn
1               5                   10                  15

Gln Xaa
```